(12) United States Patent
Adamovich et al.

(10) Patent No.: US 10,256,427 B2
(45) Date of Patent: Apr. 9, 2019

(54) EFFICIENT ORGANIC ELECTROLUMINESCENT DEVICES

(71) Applicant: Universal Display Corporation, Ewing, NJ (US)

(72) Inventors: Vadim Adamovich, Yardley, PA (US); James Esler, Yardley, PA (US); Jason Brooks, Philadelphia, PA (US); Michael S. Weaver, Princeton, NJ (US); Julia J. Brown, Yardley, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 1077 days.

(21) Appl. No.: 14/253,811

(22) Filed: Apr. 15, 2014

(65) Prior Publication Data
US 2015/0295197 A1 Oct. 15, 2015

(51) Int. Cl.
| | |
|---|---|
| C09K 11/06 | (2006.01) |
| H05B 33/14 | (2006.01) |
| H01L 51/50 | (2006.01) |
| C07D 213/02 | (2006.01) |
| C07D 401/04 | (2006.01) |
| C07D 233/54 | (2006.01) |
| C07D 235/04 | (2006.01) |
| H01L 51/00 | (2006.01) |

(52) U.S. Cl.
CPC ........ *H01L 51/5004* (2013.01); *C07D 213/02* (2013.01); *C07D 233/54* (2013.01); *C07D 235/04* (2013.01); *C07D 401/04* (2013.01); *C09K 11/06* (2013.01); *H01L 51/5016* (2013.01); *H01L 51/5024* (2013.01); *H05B 33/14* (2013.01); *H01L 51/006* (2013.01); *H01L 51/0054* (2013.01); *H01L 51/0067* (2013.01); *H01L 51/0071* (2013.01); *H01L 51/0072* (2013.01); *H01L 51/0074* (2013.01); *H01L 51/0081* (2013.01); *H01L 51/0085* (2013.01); *H01L 51/0087* (2013.01); *H01L 51/0094* (2013.01); *H01L 2251/5376* (2013.01); *H01L 2251/5384* (2013.01); *H01L 2251/552* (2013.01)

(58) Field of Classification Search
CPC ..... C09K 11/06; H05B 33/14; H01L 51/5032; H01L 51/5064; H01L 51/0032; H01L 51/5296; C07D 213/02; C07D 401/04; C07D 233/54; C07D 235/04
USPC .................. 428/690, 917; 313/504; 257/40, 257/E51.044; 546/4, 10; 548/103, 108, 548/106
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 8,685,540 | B2 * | 4/2014 | Adamovich ........ H01L 51/5016 252/301.16 |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Atzrodt et al. Angew. Chem. Int. Ed. 2007, 46, 7744-7765.*
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).

(Continued)

*Primary Examiner* — Venkataraman Balasubramanian
(74) *Attorney, Agent, or Firm* — Duane Morris LLP

(57) ABSTRACT

An OLED device includes, in order, an electron blocking layer, an organic emissive layer, and a hole blocking layer. Its organic emissive layer contains at least four components: an electron transporting compound, a host, a hole transporting compound, and an emitting compound capable of phosphorescence emission at room temperature. The emitting compound has HOMO energy level of 5.2 eV or lower and a LUMO energy level of 2.5 eV or higher.

20 Claims, 8 Drawing Sheets

(56) References Cited

U.S. PATENT DOCUMENTS

| | | | |
|---|---|---|---|
| 8,871,361 B2* | 10/2014 | Xia | C09K 11/06 257/E51.044 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Pakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2013/0153881 A1* | 6/2013 | Tokoo | H01L 51/5016 257/40 |
| 2015/0069334 A1* | 3/2015 | Xia | H01L 51/009 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-

(56) References Cited

OTHER PUBLICATIONS benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9)677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10)1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing $N^{158}C^{158}N^{158}$-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

EFFICIENT ORGANIC ELECTROLUMINESCENT DEVICES

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting device structures with deep HOMO (highest occupied molecular orbital) emitters.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a fill color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

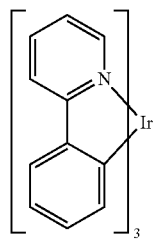

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Organic", however, does not include metal coordination complexes. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level. As used herein, a "shallower" HOMO or LUMO energy level is equivalent to a "higher" HOMO or LUMO energy level. Additionally, as used herein, a "deeper" HOMO or LUMO energy level is similar to a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In one embodiment, a device is provided with an anode, an electron blocking layer, an organic light emissive layer, a hole blocking layer, and a cathode. The device has those layers arranged in that order. The organic light emissive layer comprises a first sub-layer that includes a host compound, a first emitting compound capable of phosphorescence emission at room temperature with a HOMO of 5.2 eV or lower and a LUMO of 2.5 eV or higher, a hole transporting compound, and an electron transporting compound. Less than 5% of the light emitted from the device is comprised of light emitted from the hole transporting compound, the electron transporting compound and the host compound.

In one embodiment, the electron blocking layer is in direct contact with the organic light emissive layer and the hole blocking layer is in direct contact with the organic light emissive layer.

In one embodiment, the first sub-layer is the only layer in the organic light emissive layer.

In one embodiment, the organic light emissive layer comprises a second sub-layer, the second sub-layer includes a second host compound, a second emitting compound, a second hole transporting compound, and a second electron transporting compound. The second emitting compound is different from the first emitting compound. In one embodiment, the first host compound and the second host compound are the same, the first hole transporting compound and the second hole transporting compound are the same, and the first electron transporting compound and the second electron transporting compound are the same.

In one embodiment, the hole transporting compound and the electron transporting compound are organic compounds. In one embodiment, the hole transporting compound and the electron transporting compound are metal coordination compounds.

In one embodiment, the emitting compound has a HOMO of 5.4 eV or lower.

In one embodiment, the emitting compound comprises a transition metal complex having at least one ligand or part of the ligand if the ligand is more than bidentate selected from the group consisting of:

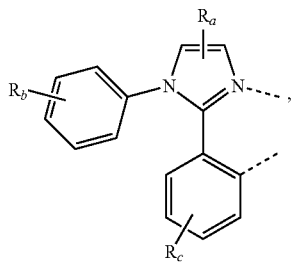

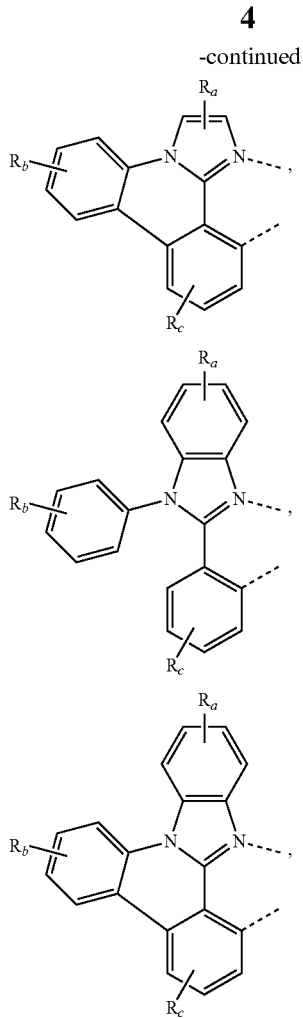

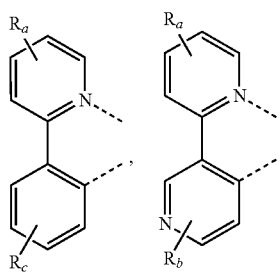

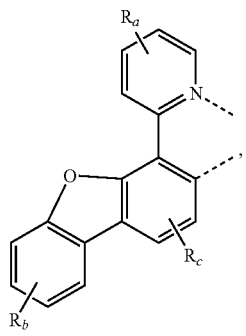

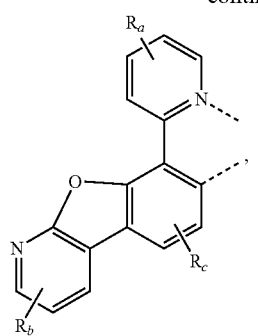
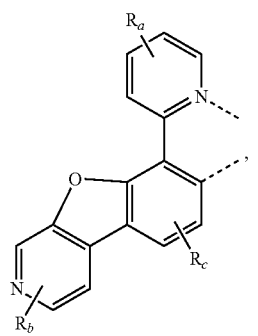
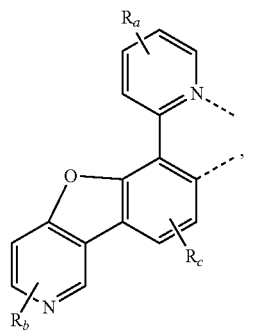
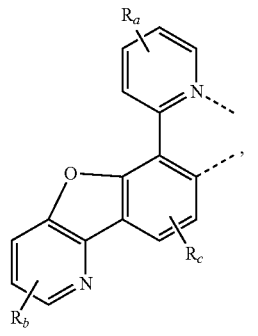
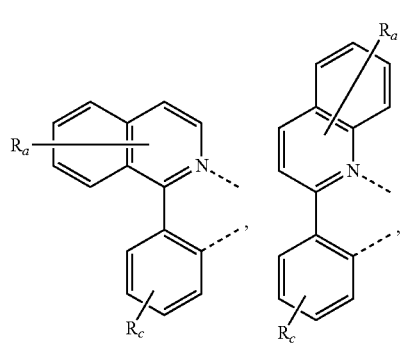
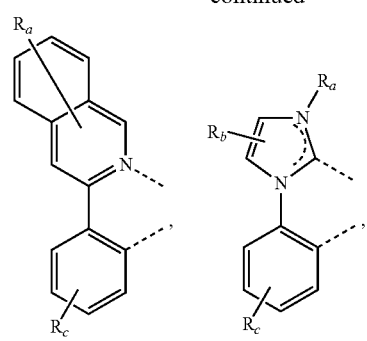
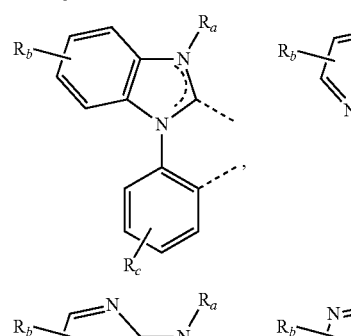
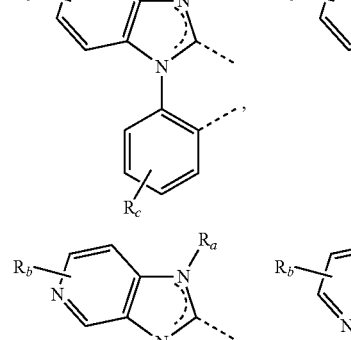
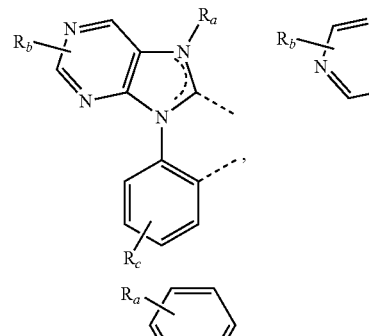
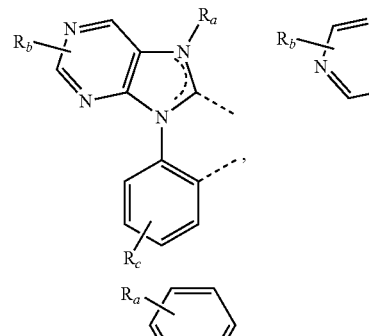

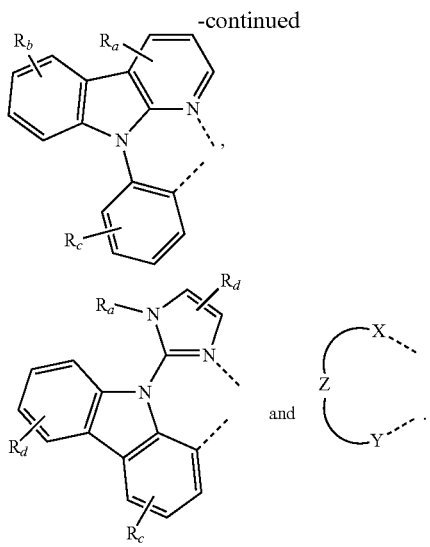

The $R_a$, $R_b$, $R_c$, and $R_d$ represents mono, di, tri, or tetra substitution, or no substitution and are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_a$, $R_b$, $R_c$, and $R_d$ are optionally joined to form a fused ring or form a multidentate ligand and at least one of $R_c$, is an electron withdrawing group. X and Y are each independently selected from group consisting of pyrazole, tetrazole, thiazole, furan and pyridine. Additionally, X and Y can be further substituted by one or more substituents selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Z is a group of formula $JR'_p R''_q$ and J is hydrogen or a metal or a non-metal, R' and R'' are independently selected from the group consisting of halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. P and q are integers between 0 and 2.

In one embodiment, at least one of $R_c$, has a Hammett constant σ greater than 0.1.

In one embodiment, the emitting compound is a Platinum tetradentate compound.

In one embodiment, the electron blocking layer has a T1 at least 0.1 eV higher than a T1 of the emitting compound and a LUMO level at least 0.1 eV higher than a LUMO level of the emitting compound or the electron transporting compound. The hole blocking layer has a T1 at least 0.1 eV higher than the T1 of the emitting compound and a HOMO level at least 0.1 eV lower than a HOMO level of the emitting compound or the hole transporting compound. The electron transporting compound has a T1 at least 0.1 eV higher than the T1 of the emitting compound and the LUMO level of the electron transporting compound is at least 0.1 eV lower than a LUMO level of the hole transporting compound. The hole transporting compound has a T1 at least 0.1 eV higher than a T1 of the emitting compound and the HOMO level of the hole transporting compound is at least 0.1 eV higher than a HOMO level of the electron transporting compound. The host compound has a T1 at least 0.1 eV higher than the T1 of the emitting compound, a. HOMO level at least 0.3 eV lower than the HOMO level of the hole transporting compound, and a LUMO level at least 0.3 eV higher than the LUMO level of the electron transporting compound.

In one embodiment, the device comprises, in order, the anode, a hole transport layer, the electron blocking layer, the organic light emissive layer, the hole blocking layer, an electron transport layer, and the cathode.

In one embodiment, the electron blocking layer has a T1 at least 0.1 eV higher than a T1 of the emitting compound.

In one embodiment, the electron blocking layer has a LUMO level at least 0.1 eV higher than a LUMO level of the emitting compound.

In one embodiment, the electron blocking layer has a LUMO level at least 0.1 eV higher than a LUMO level of the electron transporting compound.

In one embodiment, the hole blocking layer has a T1 at least 0.1 eV higher than a T1 of the emitting compound.

In one embodiment, the hole blocking layer has a HOMO level at least 0.1 eV lower than a HOMO level of the emitting compound.

In one embodiment, the hole blocking layer has a HOMO level at least 0.1 eV lower than a HOMO level of the hole transporting compound.

In one embodiment, the electron transporting compound has a T1 at least 0.1 eV higher than a T1 of the emitting compound.

In one embodiment, the electron transporting compound has a LUMO level at least 0.1 eV lower than a LUMO level of the hole transporting compound.

In one embodiment, the hole transporting compound has a T1 at least 0.1 eV higher than a T1 of the emitting compound.

In one embodiment, the hole transporting compound has a HOMO level at least 0.1 eV higher than a HOMO level of the electron transporting compound.

In one embodiment, the host compound has a T1 at least 0.1 eV higher than a T1 of the emitting compound.

In one embodiment, the host compound has a HOMO level at least 0.3 eV lower than a HOMO level of the hole transporting compound.

In one embodiment, the host compound has a LUMO level at least 0.3 eV higher than a LUMO level of the electron transporting compound.

In one embodiment, a LUMO of the electron transporting compound is higher than 2.5 eV.

In one embodiment, a HOMO level of the hole transporting compound is lower than 5.2 eV.

In one embodiment, the device has a 19.9% EQE at 1000 nits.

In one embodiment, the emitting compound is capable of red phosphorescent emission, having a peak wavelength in its emission spectrum in the range 590 nm to 700 nm.

In one embodiment, the emitting compound is capable of yellow phosphorescent emission, having a peak wavelength in its emission spectrum in the range 550 nm to 590.

In one embodiment, the emitting compound is capable of green phosphorescent emission, having a peak wavelength in its emission spectrum in the range 500 nm to 550 nm.

In one embodiment, the emitting compound is capable of blue phosphorescence emission, having a peak wavelength in its emission spectrum in the range 400 nm to 500 nm.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
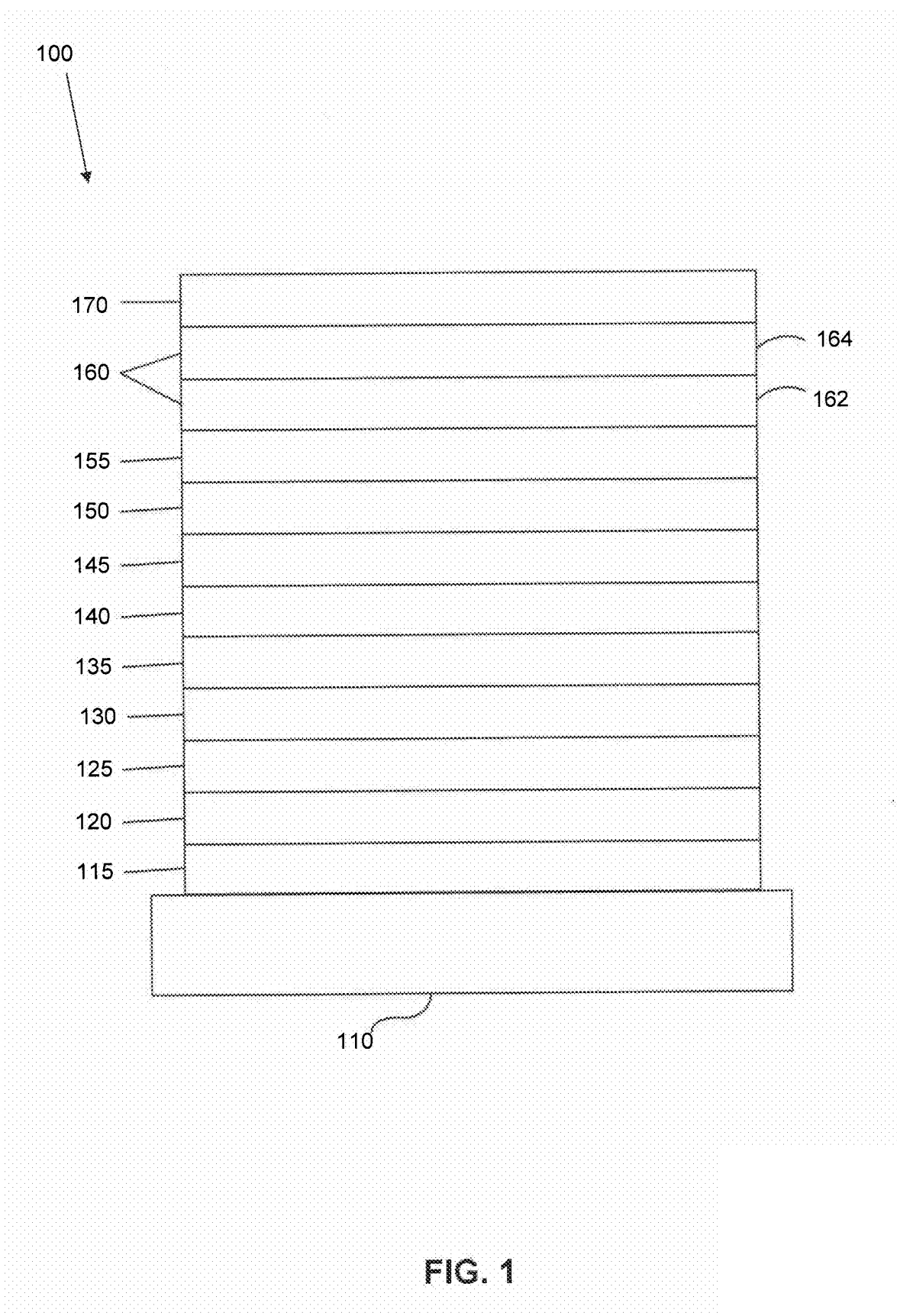
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
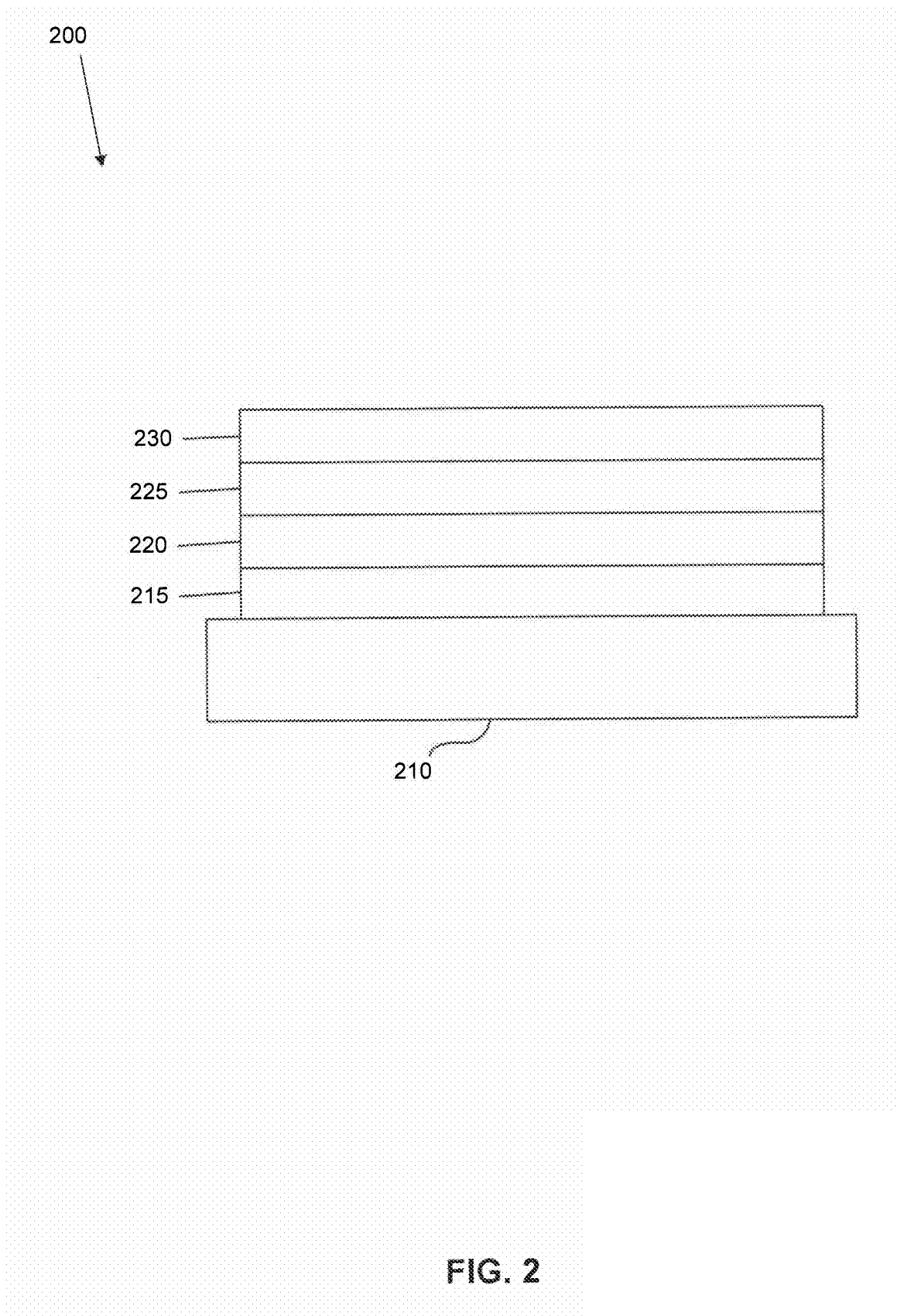
FIG. 2 shows an inverted organic light emitting (top-emitting) device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sub-layers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc, The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer, The barrier layer may incorporate an inorganic or an organic compound or both, The preferred barrier layer comprises a mixture of a polymeric material and a non-polymeric material as described in U.S. Pat. No. 7,968,146, PCT Pat. Application Nos, PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also refer to heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, the "visible spectrum" includes wavelengths in the range 400 nm to 700 nm. As used herein, "red" light corresponds to an emission spectrum with a peak wavelength in the range 590 nm to 700 nm. "Yellow" light corresponds to an emission spectrum with a peak wavelength in the range 550 nm to 590 nm. "Green" light corresponds to an emission spectrum with a peak wavelength in the range 500 nm to 550 nm. "Blue" light corresponds to an emission spectrum with a peak wavelength in the range 400 nm to 500 nm.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

Many classes of phosphorescent emissive compounds have lower HOMO and higher LUMO energy levels than the energy levels of Ir(ppy)$_3$ and its analog emissive compounds. As a non-limiting example, green emissive compounds in Pt(ppy)$_2$ family have HOMO energy levels ranging from −5.2 eV to −5.5 eV. This is around 0.1-0.4 eV lower than the HOMO energy level of Ir(ppy)$_3$ and its analog compounds. As another non-limiting example, emissive compounds in the Ir pyridyl-pyridine family have HOMO energy levels around −5.4 eV. This is about 0.6 eV lower than emissive compounds with a neutrally coordinated 5-member ring heterocycles, such as those in the phenanthridine imizdazole and phenyl imidazole families, These compounds are known as "deep HOMO emitters." As used herein, "emissive" compounds are compounds that are capable of emission under normal OLED operating conditions. Emissive compounds, however, may not emit when incorporated into a certain OLED device because of an intentional design of the OLED device. "Emitting" compounds or "emitters" are emissive compounds that contribute more than 5% to the light emitted by the OLED device.

Embodiments disclosed herein relate to OLED structures for phosphorescent emitting compounds with low HOMO and high LUMO energy levels. Of times, when an OLED with a deep HOMO emitter has a similar device arrangement as an OLED device with a shallow HOMO emitter, efficient device performance cannot be achieved. Generally, the devices disclosed herein allow for improved HOMO-LUMO level alignment due to the arrangement of the OLED layers. These devices also have efficient charge balance in the organic emissive layer as well as a minimization of emission quenching by charge carriers. Thus, as compared with devices for "shallow" HOMO emitters and other deep HOMO emitters, the OLEDS disclosed herein have a very high efficiency and longer relative lifetime.

Figure 3:
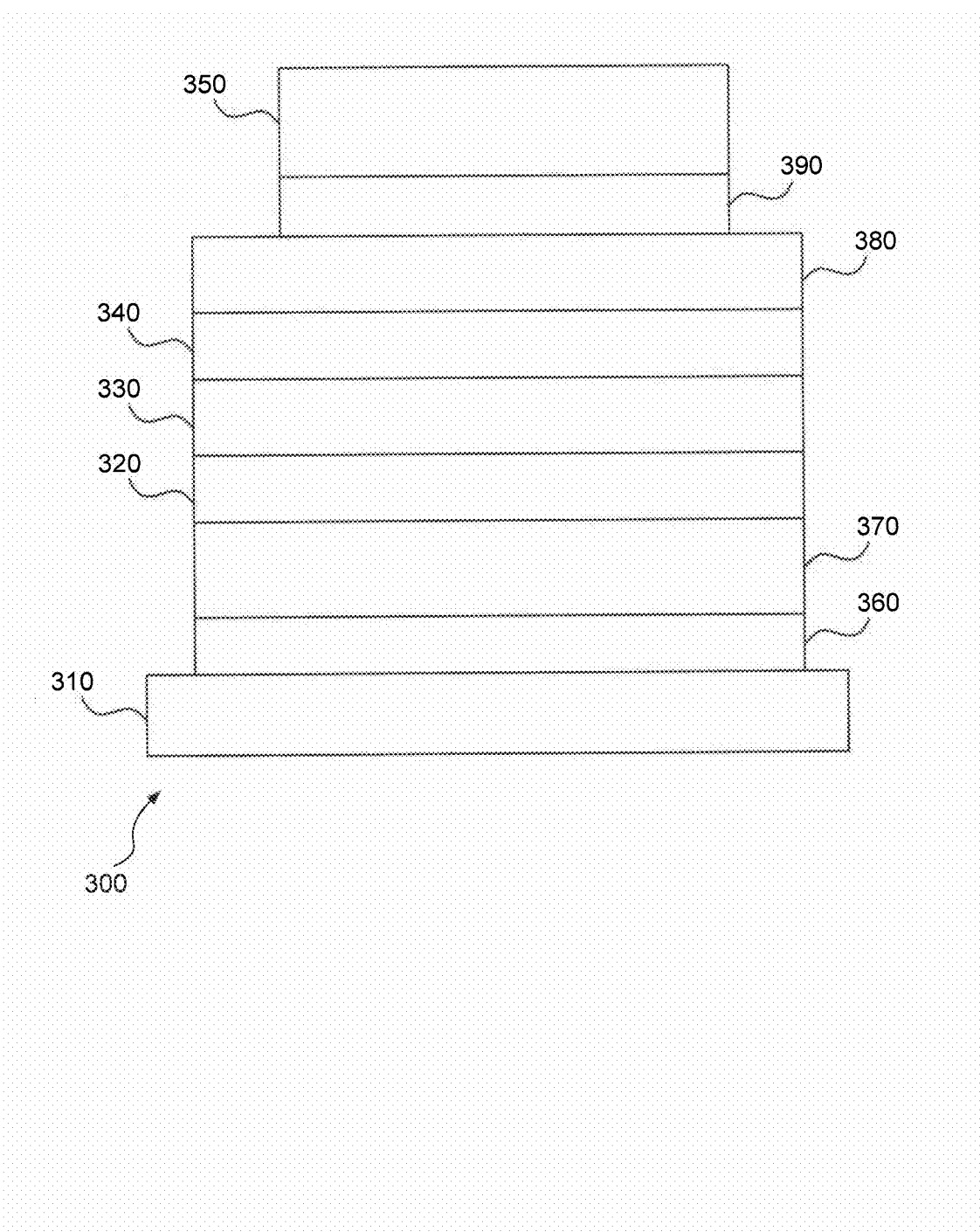
FIG. 3 shows an organic light emitting device with an electron blocking layer, an organic emissive layer, and a hole blocking layer.

Referring to FIG. 3, OLED 300 is provided according to one embodiment. OLED 300 has four layers arranged in the following order: an anode 310, an electron blocking layer 320, an organic light emissive layer 330, a hole blocking layer 340, and a cathode 350. As used herein, "in order" allows for the inclusion of other layers in between consecutively named layers as tong as the overall order of the four layers (the anode, the electron blocking layer, the organic light emissive layer, and the hole Hocking layer) remains the same. For example, as shown in FIG. 3, OLED 300 can include a hole injection layer 360 disposed between the anode 310 and the electron blocking layer 320. Additionally, OLED 300 can also optionally include other layers such as a hole transport layer 370, an electron injection layer 380, and an electron transport layer 390. The OLED can be structured such that order "begins" at the top of the OLED (with the anode as shown in FIG. 2 in a top-emitting device) or "begins" at the bottom of the OLED (with the anode on the bottom as shown in FIG. 3).

Figure 3A:
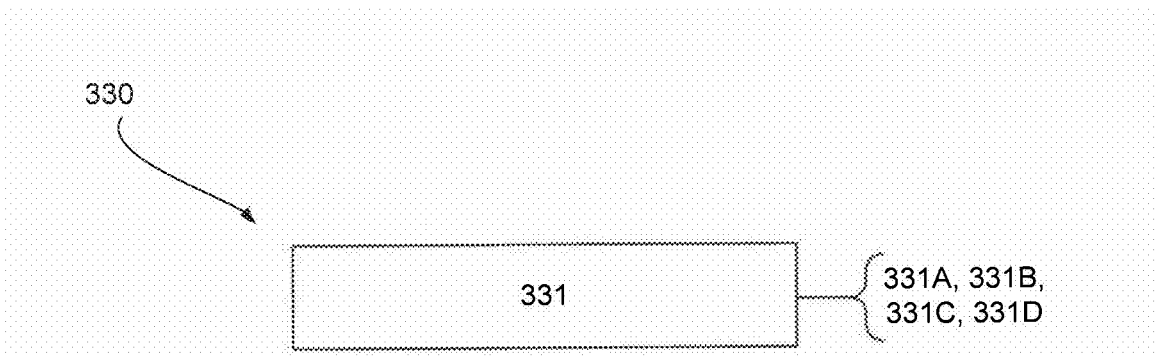
FIGS. 3A and 3B show embodiments of the organic emissive layer of OLED in FIG. 3.

The organic light emissive layer 330 of OLED 300 is shown in further detail in FIG. 3A. Organic light emissive layer 330 includes a first sub-layer 331. First sub-layer 331 is comprised of a host compound 331A, a first emitting compound 331B, a hole transporting compound 331C, and an electron transporting compound 331D. While FIG. 3A depicts only four components in the first sub-layer, first sub-layer 331 may optionally contain additional components, such as dopants and sensitizers as known in the art.

The first emitting compound 331B is capable of phosphorescence emission at room temperature and has a HOMO level of 5.2 eV or lower, preferably 5.4 and lower, including 5.5 eV, 5.6 eV, 5.7 eV, and 5.8 eV. The first emitting compound 331B has a LUMO of 2.5 eV or higher. Additionally, the first emitting compound may be capable of red, yellow, green, or blue phosphorescence emission at room temperature.

One way of determining HOMO and LUMO energy levels is through solution cyclic voltammetry and differential pulsed voltammetry. In one aspect, a CH Instruments model 6201B potentiostat may be used with an anhydrous dimethylformamide as the solvent and Tetrabutylammonium hexafluorophosphate as the supporting electrolyte. Glassy carbon, platinum, and silver wires may be used as the working, counter and reference electrodes, respectively. Electrochemical potentials are referenced to an internal ferrocene-ferroconium redox couple (Fc/Fc+) by taking peak potential differences from differential pulsed voltammetry. The corresponding HOMO and LUMO energies are then determined by referencing the cationic and anionic redox potentials to ferrocene (4.8 eV vs. vacuum). Examples of energy levels determined in this way or similar ways can be found in Fink, R.; Heischkel, Y.; Thelakkat, M.; Schmidt, H.-W. *Chem. Mater.* 1998, 10, 3620-3625 and Pommerehne, J.; Vestweber, H.; Guss, W.; Mahrt, R. F.; Bassler, H.; Porsch, M.; Daub, J. *Adv. Mater.* 1995, 7, 551. Unless otherwise specified, HOMO and LUMO energy levels described in this application are determined as described in this paragraph.

In some embodiments, the first emitting compound 331B may be a Platinum tetradentate compound. These include but are not limited to:

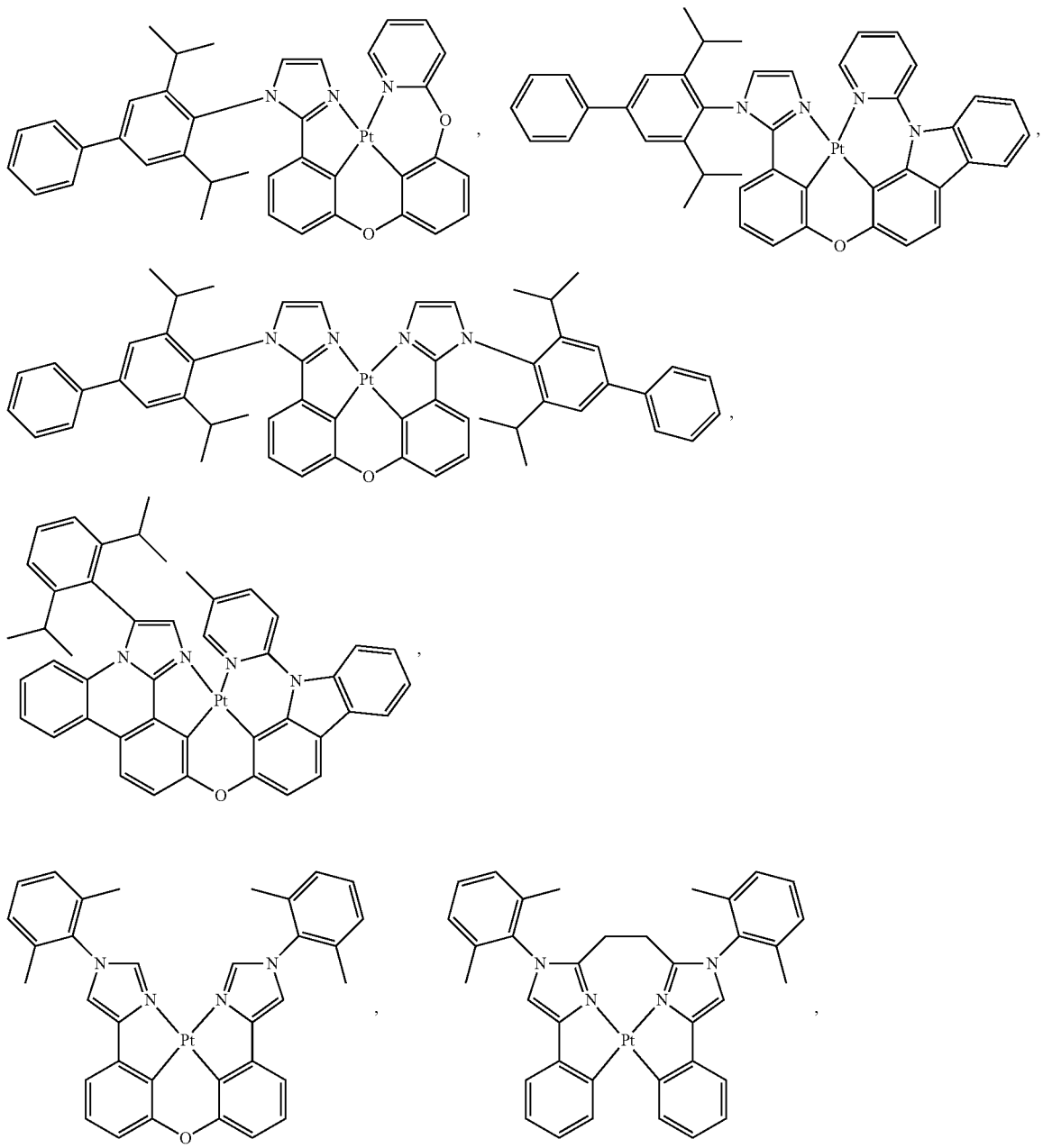

-continued
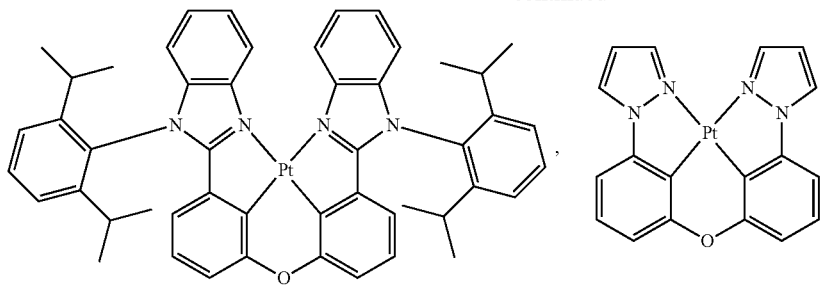
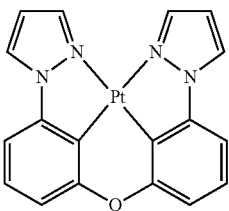
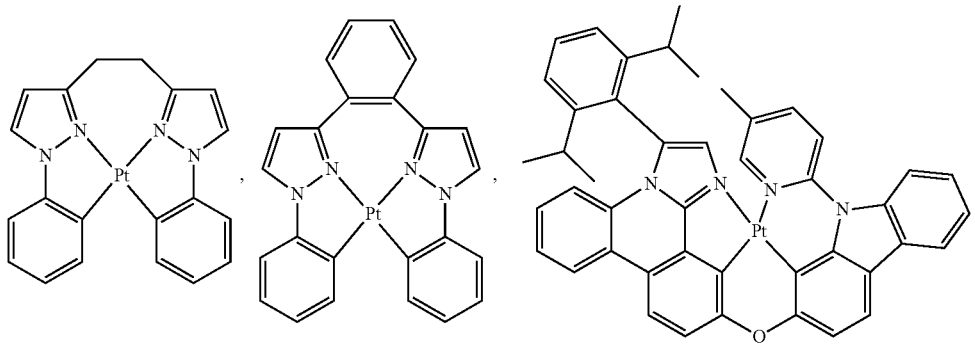
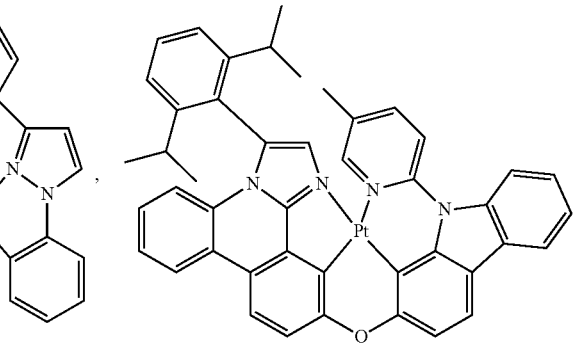
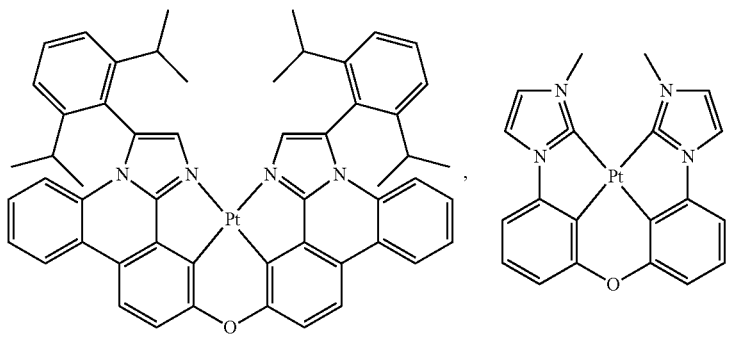
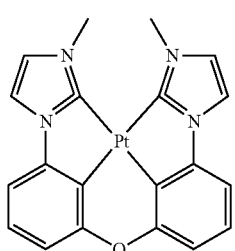
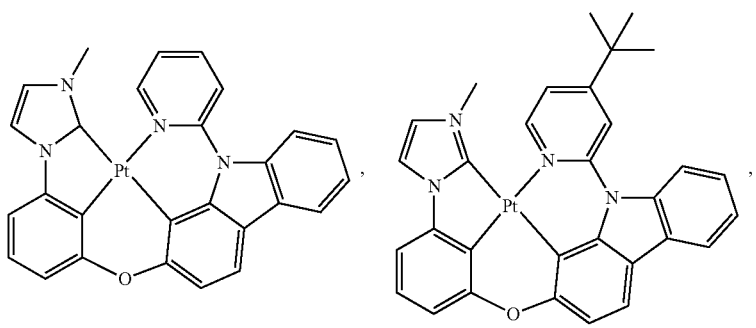
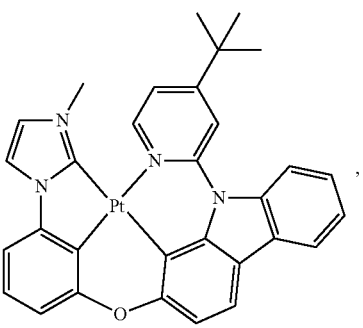
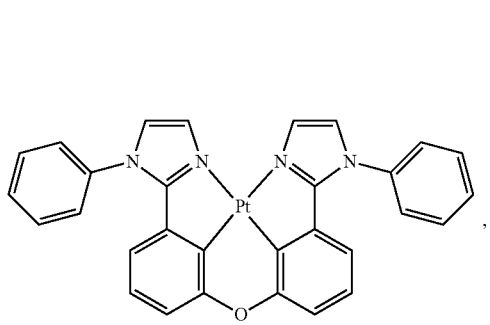
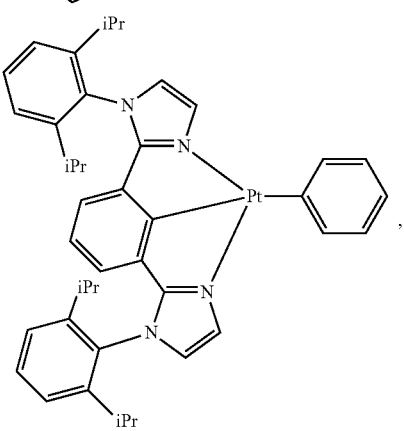

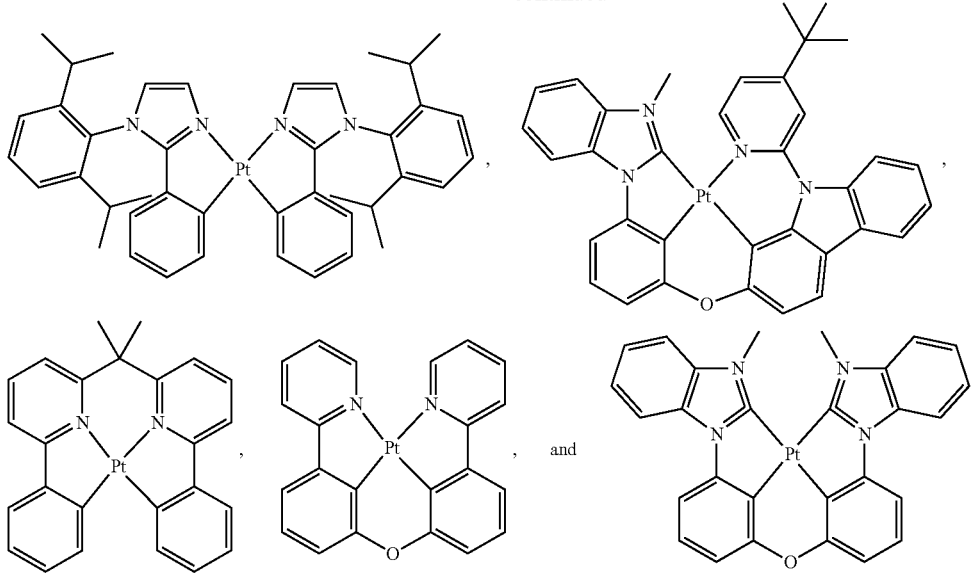
In some embodiments, the first emitting compound 331 B may comprise a transition metal complex. This complex includes at least one ligand, or part of a ligand (if the ligand is more than bidentate), that can be selected from the following groups:
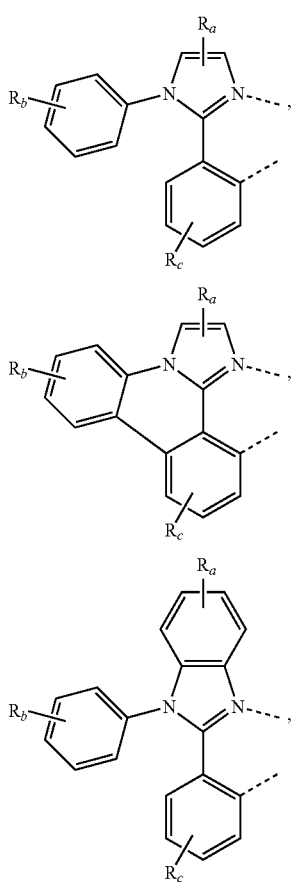
-continued
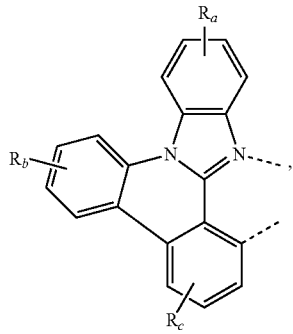
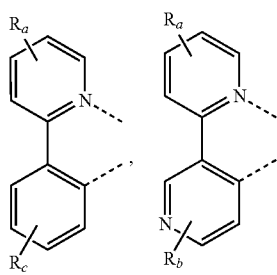
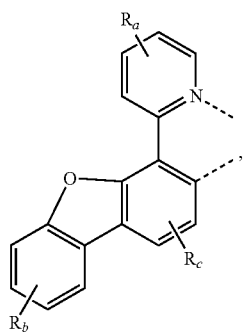

-continued
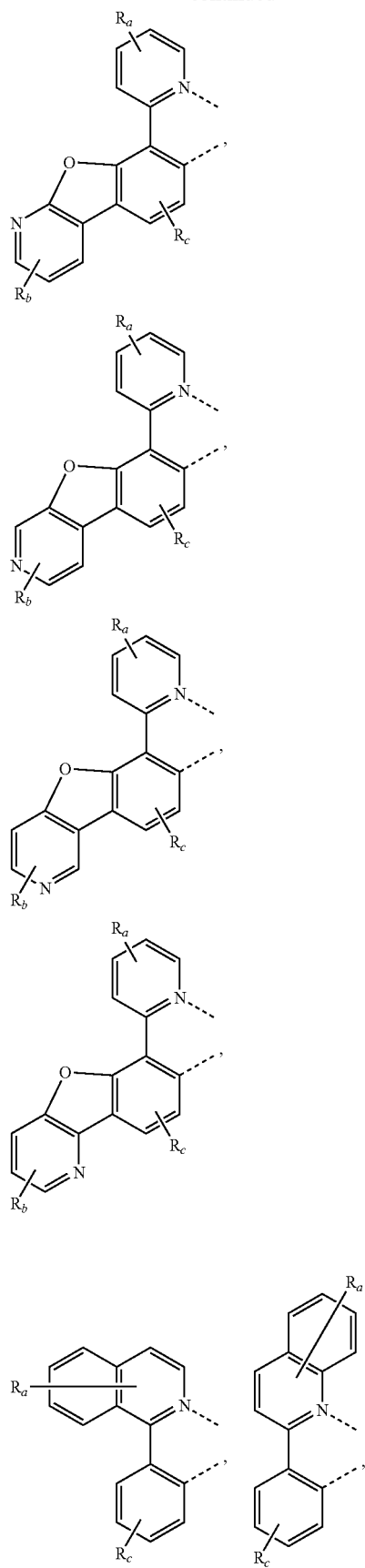
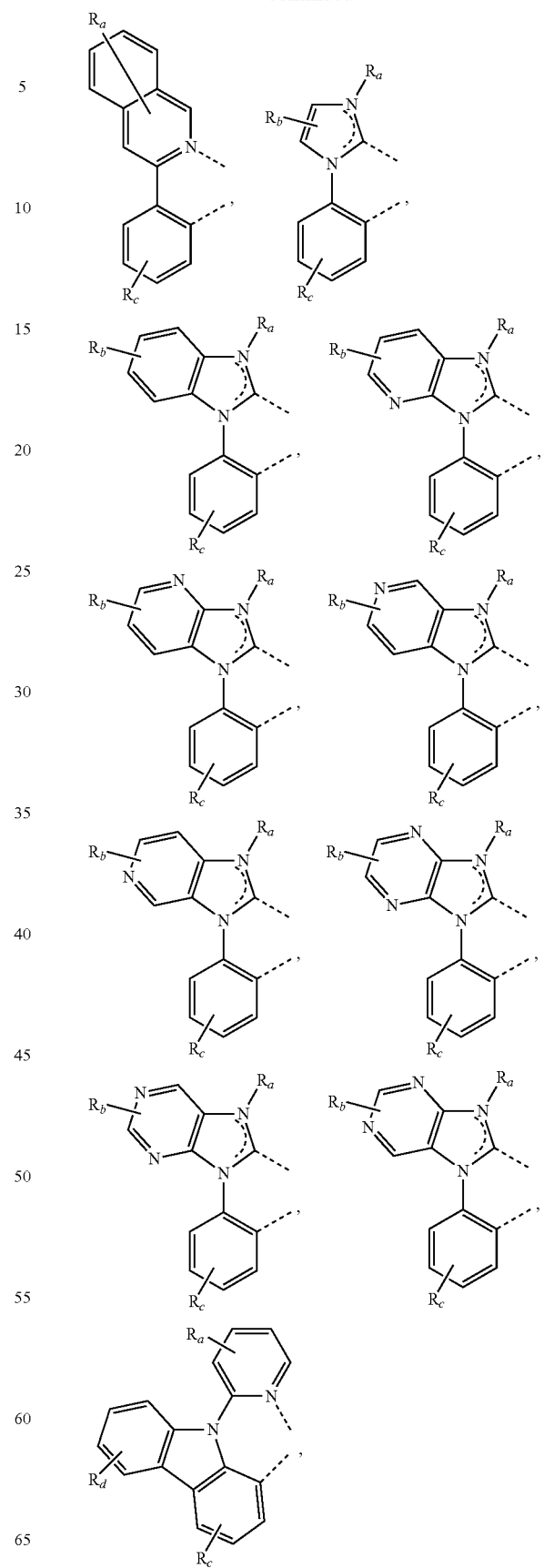

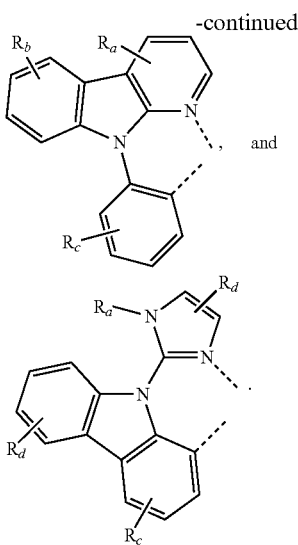

$R_a$, $R_b$, $R_c$, and $R_d$ may represent mono, di, tri, tetra or no substitution. Each are independently selected from a group of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, or a combination of them. In one embodiment, two adjacent substituents of $R_a$, $R_b$, $R_c$, and $R_d$ may be joined to form a fused ring or a multidentate ligand. As used herein, "joined" means that adjacent groups are linked to each other by a chemical bond. In other embodiments, adjacent substituents are not joined.

At least one of the $R_c$ is preferably an electron withdrawing group with a Hammett constant of at least 0.1, preferably of at least 0.2, and more preferably of at least 0.3. The Hammett constant of a substituent is defined on the basis of the ionization constant of a substituted benzoic acid at 25 C as follows:

$$\sigma_x = \log K_X - \log K_H \quad (1)$$

where $K_H$ is the ionization constant for benzoic acid in water at 25 C and $K_x$ is the corresponding constant for a meta or para-substituted benzoic acid. A Hammett constant can be used to successfully predict equilibrium and rate constants in solution. Further information regarding Hammett constants can be found in *A Survey of Hammett Substituent Constants and Resonance and Field Parameters*, Chem. Rev. 1991, 91 165-195.

In other embodiments, the transition metal complex of the emitting compound may include at least one ligand, or part of a ligand (if the ligand is more than bidentate), that has the general structure

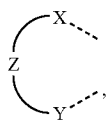

X and Y are each independently selected from a group including pyrazole, tetrazole, thiazole, furan, and pyridine. Additionally, X and Y can each be further substituted by hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Z may have the formula $JR'_pR''_q$. In this embodiment, J may be a hydrogen, metal, or non-metal and R' and R'' are independently selected from alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. P and Q are integers and can range from 0 to 2.

Specific examples of the ligand include but are not limited to:

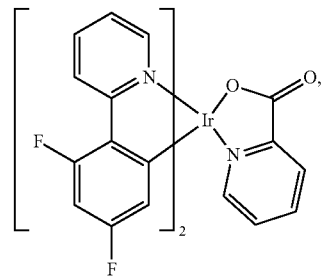

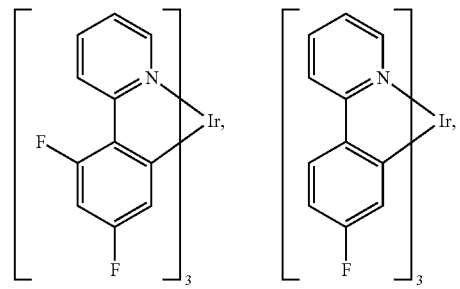

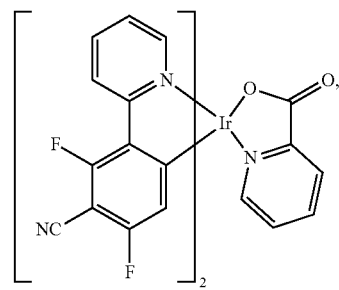

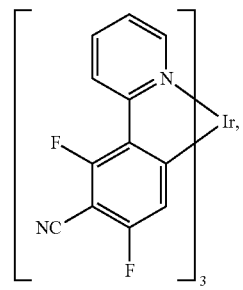
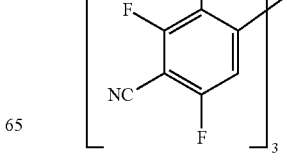

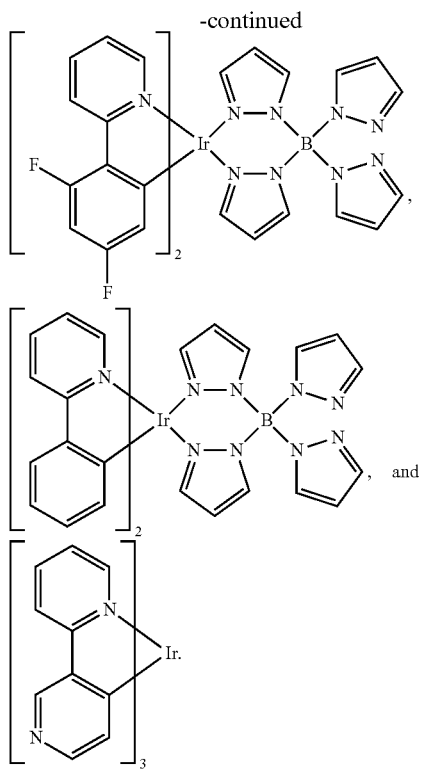

Preferably, in normal operating conditions of luminance 1,000 nits, less than 5% of the light emitted from OLED 300 is comprised of light emitted from the hole transporting compound, light emitted from the electron transporting compound, and light emitted from the host compound. More preferably, at least 95% of light emitted from OLED 300 comes from the first emitting compound 331B.

Figure 3B:
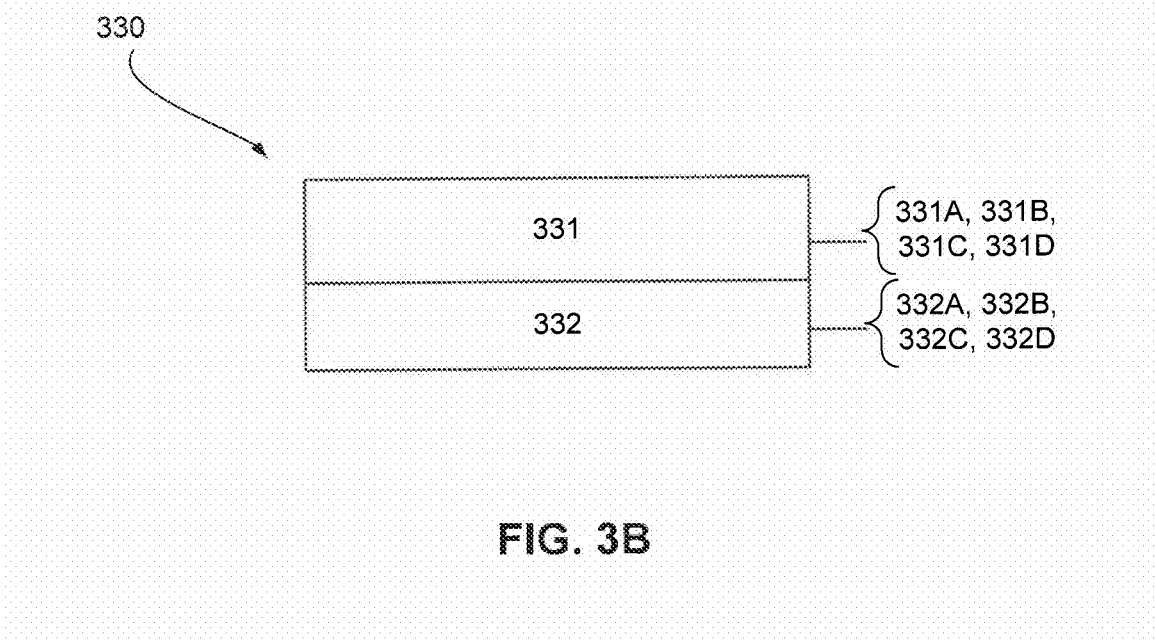

In some embodiments, organic light emissive layer 330 may include a second sub-layer 332. This is shown in FIG. 3B. This embodiment may be used for an OLED having a broad spectrum light output. An emissive layer with two or more sub-layers might be structured, for example, as having different emissive dopants in different sub-layers in order to obtain a device with broad spectrum or white emission. Second sub-layer 332 includes a second host compound 332A, a second emitting compound 332B, a second hole transporting compound 332C, and a second electron transporting compound 332D. Preferably, the second emitting compound 332B is different from the first emitting compound 331B. However, it may be the same compound. Additionally, the second emitting compound 332B may or may not be a deep HOMO emitter.

Where an emissive layer has multiple emissive sub-layers, the emissive layer is considered to be "in direct contact" with another layer, such as a blocking layer, if any of the emissive sub-layers is in direct contact with that other layer.

Preferably, the second host compound 332A, the second hole transporting compound 332C, and the second electron transporting compound 332D are the same compounds as their respective counterparts in the first sub-layer 331. In one embodiment, however, they are different compounds from their respective counterparts.

Hole transporting compounds 331A and 332A and electron transporting compounds 331B and 332B can be organic compounds. Alternatively, hole transporting compounds and electron transporting compounds can be emissive but non-emitting metal coordination compounds. Hole transporting compounds and electron transporting compounds do not have to be the same type of compounds. For example, hole transporting compound can be an organic compound while electron transporting compound can be a metal coordination compound. Additionally, embodiments in which there are more than two sub-layers in the organic emissive layer are also envisioned and encompassed in this work.

In either embodiment of the organic emissive layer 330, with one or more than one sub-layers, the hole blocking layer 340 may be in direct contact with the organic emissive layer 330 and the electron blocking layer 320 may be in direct contact with the organic emissive layer 330. As used herein, "direct contact" means there is no additional layer in between the two named layers. In embodiments with two or more sub-layers in the organic emissive layer, such as the one depicted in FIG. 3B, the organic emissive layer is considered to be in "direct contact" with the hole blocking layer and the electron blocking layer as long as one sub-layer is in direct contact with one of the electron blocking and the hole blocking layer. Alternatively, embodiments in which the hole blocking layer 340 and the electron blocking layer are not in direct contact with the organic emissive layer 330 are also envisioned.

The use of an emissive layer with a hole transporting compound and an electron transporting compound may favorably allow recombination across multiple sub-layers. In many conventional phosphorescent OLED devices, it is believed that electron transport in the emissive layer is due primarily to the host, and hole transport layer in the emissive layer is due primarily due to the phosphorescent emitter. Separate electron and hole transport materials in the emissive layer, as described herein, are often not present. Additionally, doping an emissive layer with both electron and hole transporting compounds may result in multiple leakage issues not normally present in an OLED because often times, only one type of charge carrier is capable of crossing the organic emissive layer. In the dual-doped structures described herein, both hole and electron leakage from the emissive layer may be an issue, which is unusual. The use of both electron and hole blocking layer may mitigate such leakage issues. Blocking layers often have some undesirable effects, such as an increase in drive voltage, and one of skill in the art would not normally want to use both electron and hole blocking layers as is described in embodiments herein.

The relationships, including energy relationships, between the emitting compound and the other compounds in the OLED will now be discussed. In one embodiment, OLED 300 may have all of these energy relationships, and it preferably does. In other embodiments, OLED 300 may have only one or a combination of these relationships.

As used herein, "T1" refers to the triplet energy level of the compound or layer. One method of determining triplet energy is by using the highest phosphorescent energy peak in an organic solvent glass at 77° K. Unless otherwise specified, triplet energy levels described in this application are determined as described in this paragraph. A preferred solvent used is 2-MeTHF.

While some concepts are described herein with respect to only one of the embodiments for a phosphorescent device, one of skilled in the art can readily understand that these concepts can also be applied to the other embodiments. Similarly, any suitable emission principles may be implemented by the compounds and devices disclosed herein, including delayed fluorescence, thermally activated delayed fluorescence, upconversion, downconversion, and the like.

Electron Transporting Compound

An electron transporting compound in the organic emissive layer is a compound that, when combined with the other materials of the emissive layer, has a concentration and relative energy levels such that it is primarily responsible for electron transport in the emissive layer. Potential criteria for an appropriate compound include compound's T1, LUMO, and HOMO levels.

In one embodiment, the electron transporting compound has a T1 that is at least 0.1 eV higher than the T1 of the emitting compound, preferably at least 0.2 eV or 0.3 eV higher. It has a LUMO level that is at least 0.1 eV lower than the LUMO level of the hole transporting compound, preferably at least 0.2 eV or 0.3 eV lower. In one embodiment, electron transporting compounds with a LUMO level higher than 2.5 eV may also be used.

Hole Transporting Compound

A hole transporting compound in the organic emissive layer is a compound that, when combined with the other materials of the emissive layer, has a concentration and relative energy levels such that it is primarily responsible for hole transport in the emissive layer. Potential criteria for an appropriate compound include the compound's T1, LUMO, and HOMO levels.

In one embodiment, the hole transporting compound has a T1 that is at least 0.1 eV higher than a T1 of the emitting compound, more preferably at least 0.2 eV or 0.3 eV higher. It has a HOMO level that is at least 0.1 eV higher than the HOMO level of the electron transporting compound, preferably 0.2 eV or 0.3 eV higher. In one embodiment, hole transporting compounds with a HOMO level lower than 5.2 eV may also be used.

Host:

In one embodiment, the host compound has a T1 that is at least 0.1 eV higher than the T1 of the emitting compound, preferably at least 0.2 eV or 0.3 eV higher. It has a HOMO level that is at least 0.3 eV lower than the HOMO level of the hole transporting compound, preferably at least 0.4 eV or 0.5 eV lower. It has a LUMO level that is at least 0.3 eV higher than the LUMO level of the electron transporting compound, preferably at least 0.4 eV or 0.5 eV higher.

Examples of the host material are not particularly limited, and any metal coordination complexes or organic compounds may be used as long as the triplet energy of the host is larger than that of the dopant. While the Table 1 below categorizes host materials as preferred for devices that emit various colors, any host material may be used with any dopant so long as the triplet criteria is satisfied. Additionally, while the materials described here and in Table 1 generally describe materials that may be used as hosts, these materials may be limited based on other characteristics, such as energy levels, discussed elsewhere in this work.

Examples of metal complexes used as host are preferred to have the follow'ng general formula:

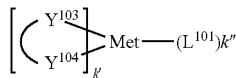

Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

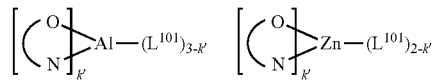

(O—N) is a bidentate ligand, having metal coordinated to atoms O and N.

In another aspect, Met is selected from Ir and Pt.

In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

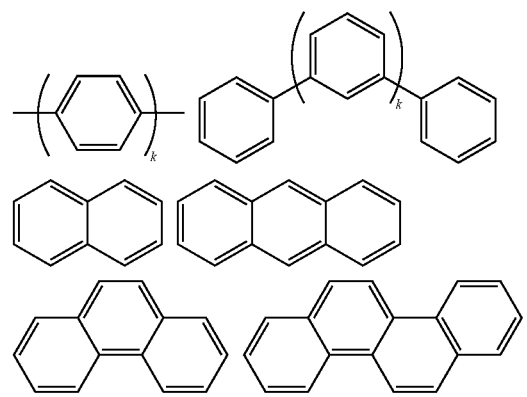

-continued

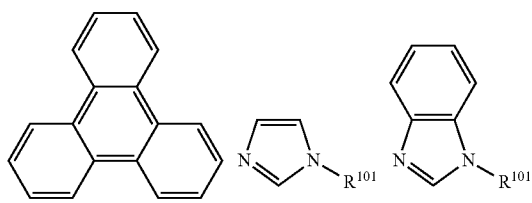

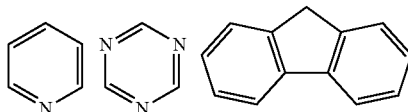

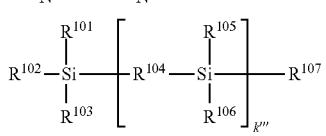

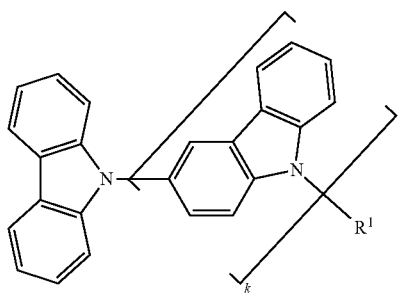

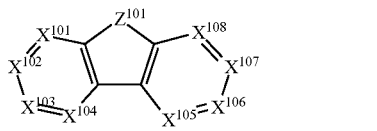

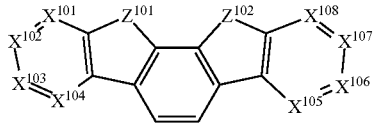

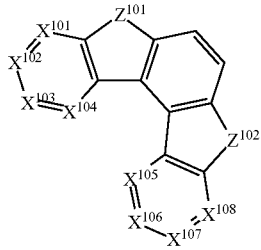

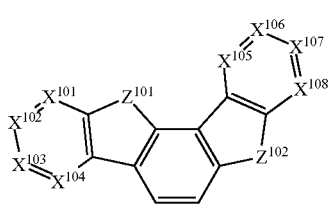

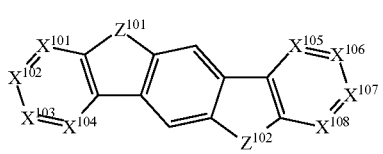

-continued

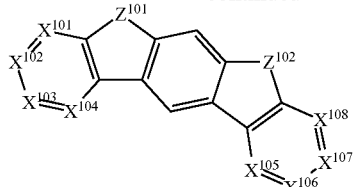

$R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 1 to 20; k''' is an integer from 0 to 20.
$X^{101}$ to $X^{108}$ is selected from C (including CH) or N.
$Z^{101}$ and $Z^{102}$ is selected from $NR^{101}$, O, or S.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Hole Injection Layer/Hole Transport Layer

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

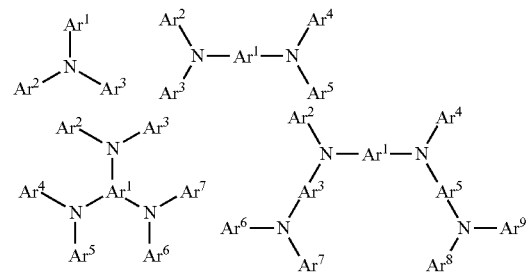

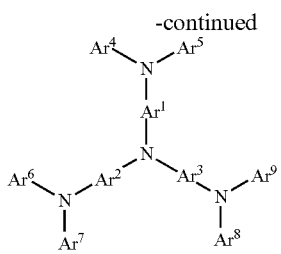

Each of Ar¹ to Ar⁹ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, phosphino, and combinations thereof.

In one aspect, Ar¹ to Ar⁹ is independently selected from the group consisting of:

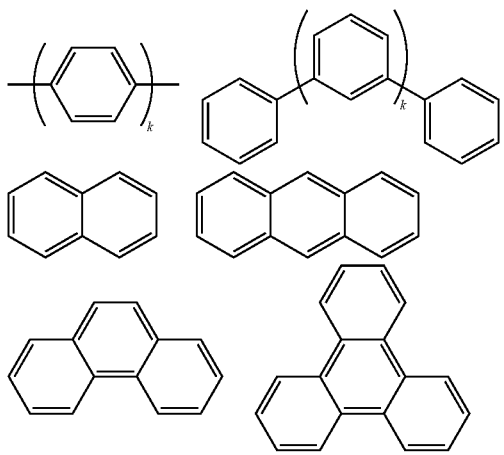

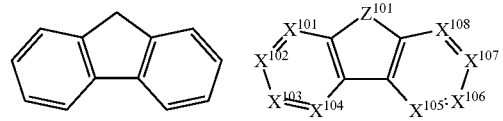

k is an integer from 1 to 20; $X^{101}$ to $X^{108}$ is C (including CH) or N; $Z^{101}$ is NAr¹, O, or S; Ar¹ has the same group defined above.

Examples of metal complexes used in HIL or HTL include, but not limit to the following general formula:

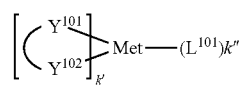

Met is a metal; ($Y^{101}$-$Y^{102}$) is a bidentate ligand, $Y^{101}$ and $Y^{102}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative.

In another aspect, ($Y^{101}$-$Y^{102}$) is a carbene ligand.

In another aspect, Met is selected from Ir, Pt, Os, and Zn.

In a further aspect, the metal complex has a smallest oxidation potential in solution vs. Fc⁺/Fc couple less than about 0.6 V.

Electron Transport Layer:

Electron transport layer (ETL) may include a material capable of transporting electrons.

Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

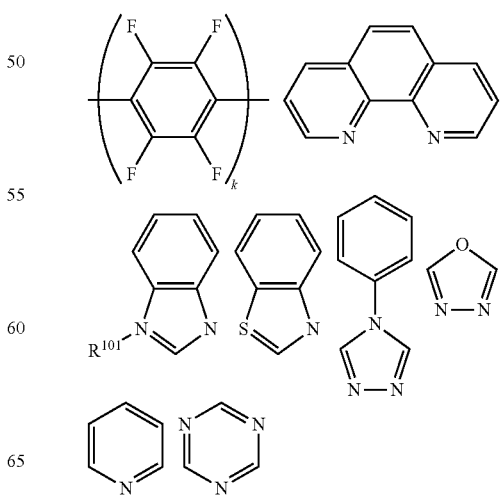

-continued

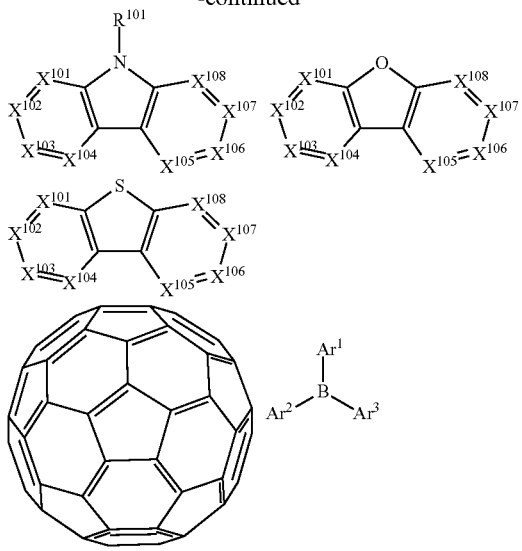

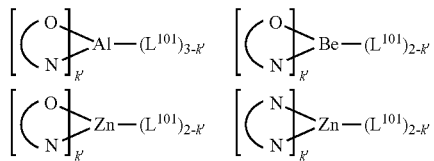

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials. While the materials in Table 1 generally describe materials that may be used in OLEDs, these materials and its applicability as a certain layer may be limited based on other characteristics, such as energy levels, discussed elsewhere in this work.

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

TABLE 1
| MATERIAL | EXAMPLES OF MATERIAL | PUBLICATIONS |
|---|---|---|
| | Hole injection materials | |
| Phthalocyanine and porphryin compounds | 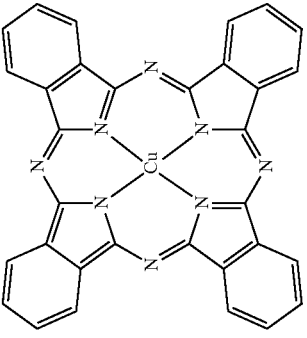 | Appl. Phys. Lett. 69, 2160 (1996) |
| Starburst triarylamines | 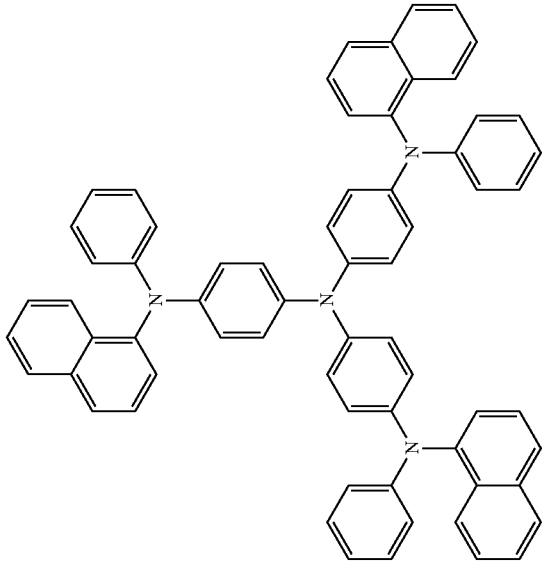 | J. Lumin. 72-74, 985 (1997) |
| $CF_x$ Fluorohydrocarbon polymer |  | Appl. Phys. Lett. 78, 673 (2001) |

TABLE 1-continued
| MATERIAL | EXAMPLES OF MATERIAL | PUBLICATIONS |
|---|---|---|
| Conducting polymers (e.g. PEDOT:PSS, polyaniline, polypthiophene) | | Synth. Met. 87, 171 (1997) WO2007002683 |
| Phosphonic acid and silane SAMs | | US2003162053 |
| Triarylamine or polythiophene polymers with conductivity dopants | | EP1725079A1 |
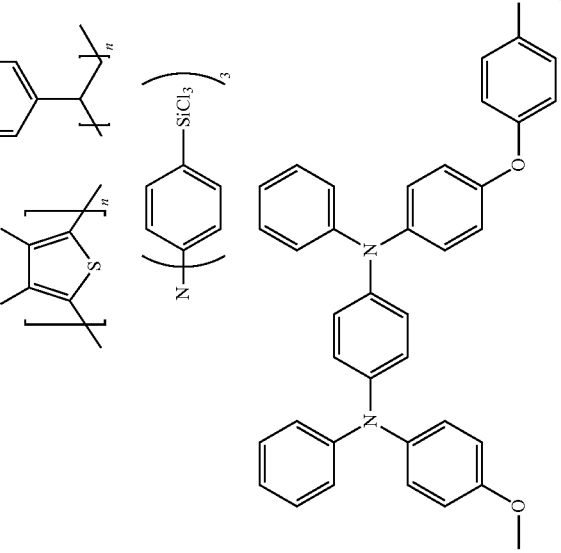
and TABLE 1-continued
| MATERIAL | EXAMPLES OF MATERIAL | PUBLICATIONS |
|---|---|---|
| |    + MoO$_x$ | US20050123751 SID Symposium Digest, 37, 923 (2006) WO2009018009 |
| Organic compounds with conductive inorganic compounds, such as molybdenum and tungsten oxides | | |

TABLE 1-continued
| MATERIAL | EXAMPLES OF MATERIAL | PUBLICATIONS |
|---|---|---|
| n-type semiconducting organic complexes | 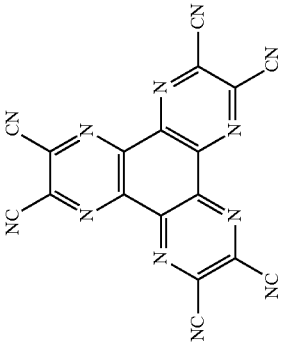 | US20020158242 |
| Metal organometallic complexes | 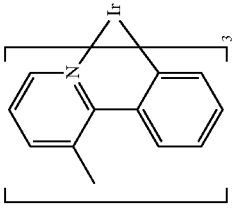 | US20060240279 |
| Cross-linkable compounds | 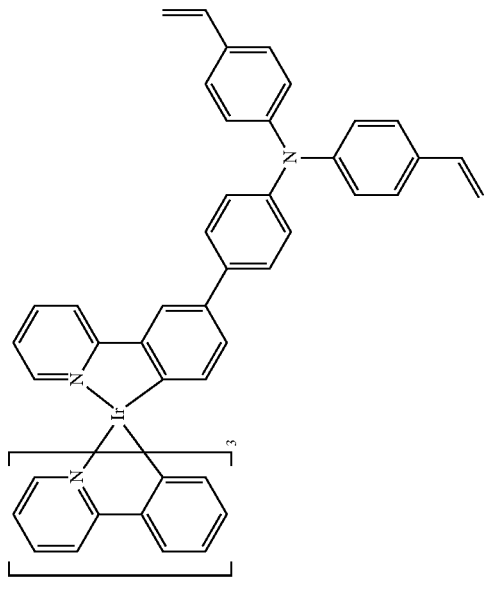 | US20080220265 |

TABLE 1-continued
| MATERIAL | EXAMPLES OF MATERIAL | PUBLICATIONS |
|---|---|---|
| Polythiophene based polymers and copolymers | 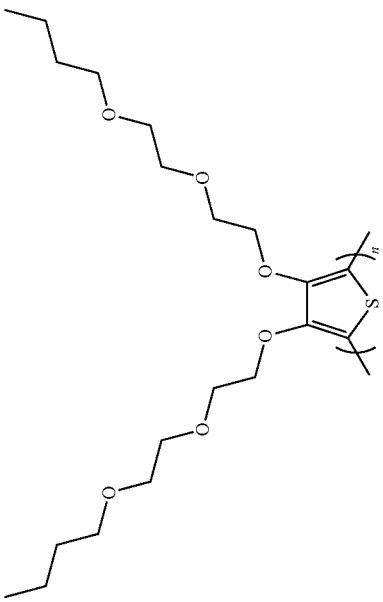 | WO2011075644 EP2350216 |
| Hole transporting materials | | |
| Triarylamines (e.g, TPD, α-NPD) | 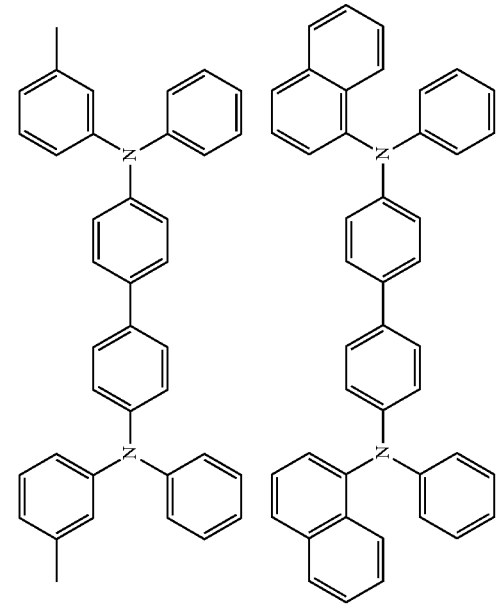 | Appl. Phys. Lett. 51, 913 (1987)<br><br>U.S. Pat No. 5,061,569 |

TABLE 1-continued
| MATERIAL | EXAMPLES OF MATERIAL | PUBLICATIONS |
|---|---|---|
| | 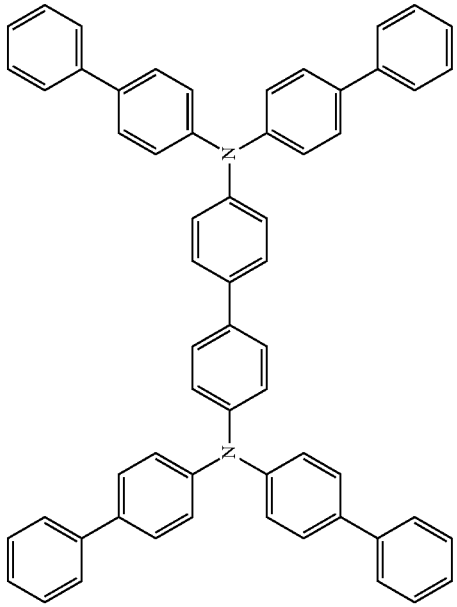 | EP650955 |
| | 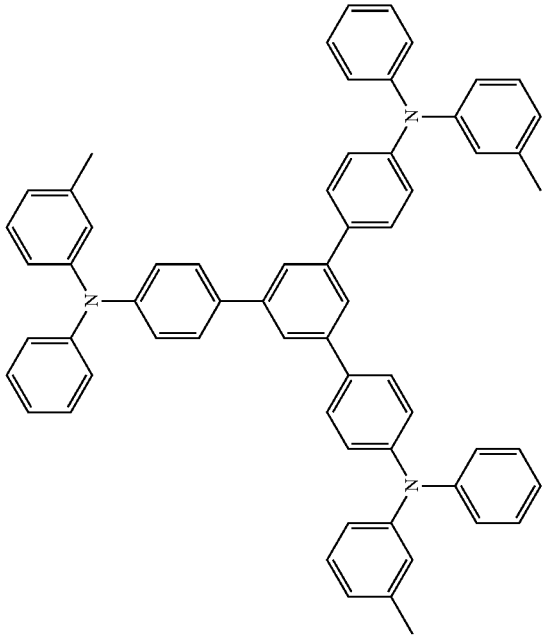 | J. Mater. Chem. 3, 319 (1993) |

TABLE 1-continued
| MATERIAL | EXAMPLES OF MATERIAL | PUBLICATIONS |
|---|---|---|
| | 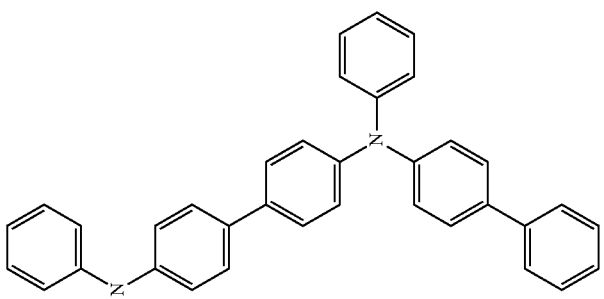 | Appl. Phys. Lett. 90, 183503 (2007) |

TABLE 1-continued
| MATERIAL | EXAMPLES OF MATERIAL | PUBLICATIONS |
|---|---|---|
| Triaylamine on spirofluorene core |  | Appl. Phys. Lett. 90, 183503 (2007) |
| | 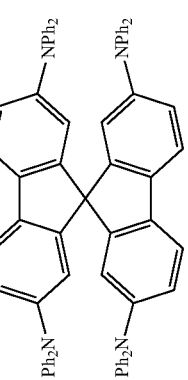 | Synth. Met. 91, 209 (1997) |

| MATERIAL | EXAMPLES OF MATERIAL | PUBLICATIONS |
| --- | --- | --- |
| Arylamine carbazole compounds | 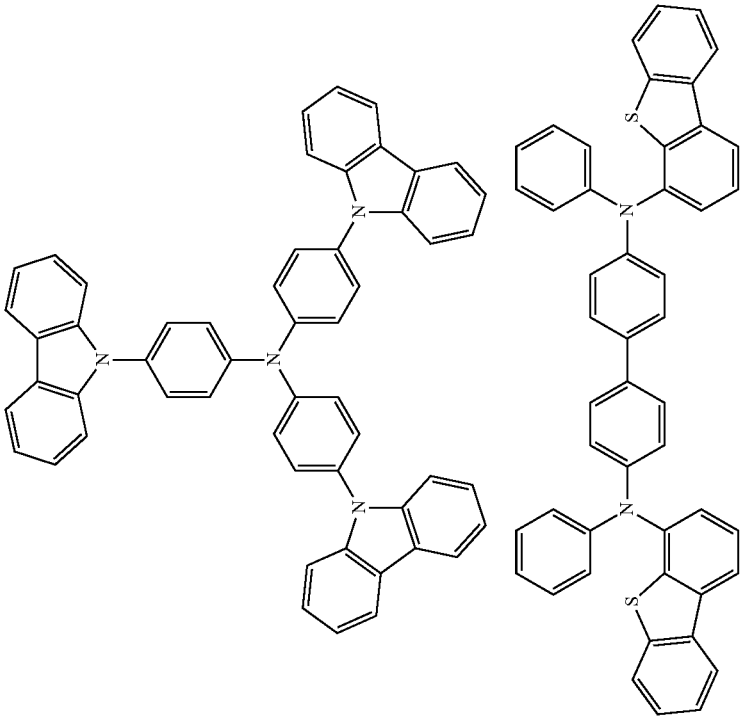 | Adv. Mater. 6, 677 (1994), US20080124572 |
| Triarylamine with (di)benzothiophene/ (di)benzofuran | | US20070278938, US20080106190 US20110163302 |

TABLE 1-continued
| MATERIAL | EXAMPLES OF MATERIAL | PUBLICATIONS |
|---|---|---|
| Indolocarbazoles | 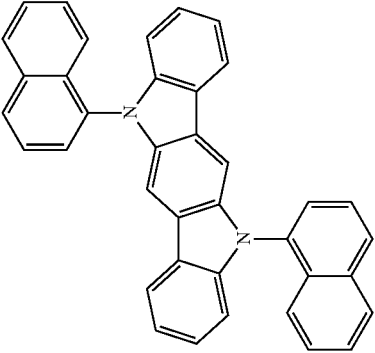 | Synth. Met. 111, 421 (2000) |
| Isoindole compounds | 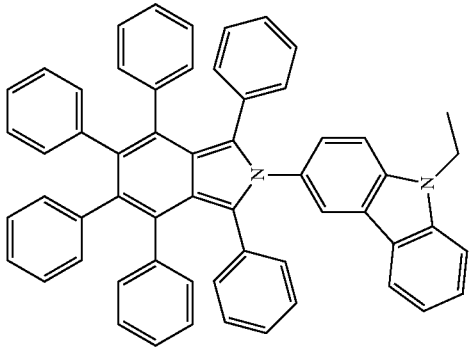 | Chem. Mater. 15, 3148 (2003) |

TABLE 1-continued
| MATERIAL | EXAMPLES OF MATERIAL | PUBLICATIONS |
|---|---|---|
| Metal carbene complexes | 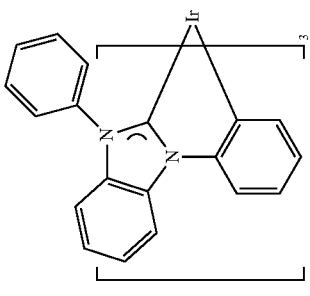 | US20080018221 |
| Phosphorescent OLED host materials | | |
| Red hosts | | |
| Arylcarbazoles | 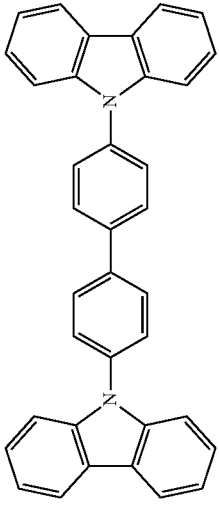 | Appl. Phys. Lett. 78, 1622 (2001) |
| Metal 8-hydroxyquinolates (e.g., Alq$_3$, BAlq) | 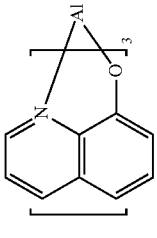 | Nature 395, 151 (1998) |
| | 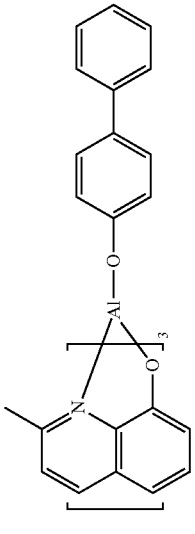 | US20060202194 |

| MATERIAL | EXAMPLES OF MATERIAL | PUBLICATIONS |
|---|---|---|
| | 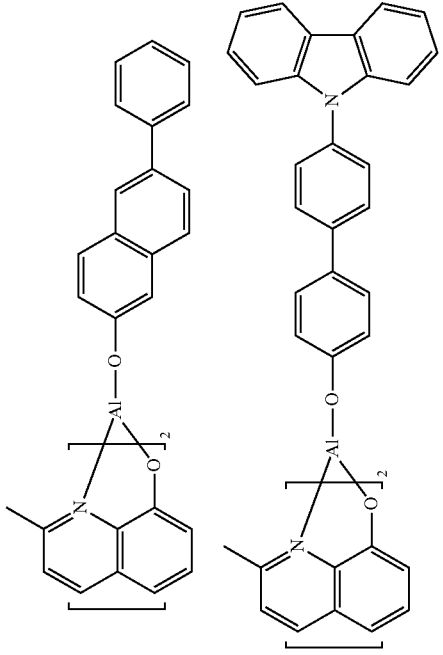 | WO2005014551 |
| | 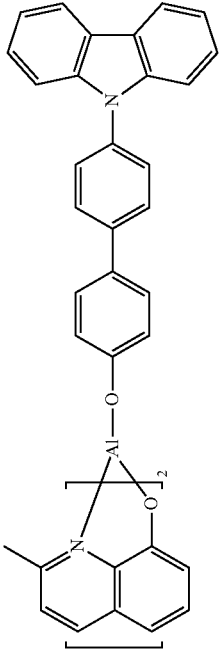 | WO2006072002 |
| Metal phenoxybenzothiazole compounds | 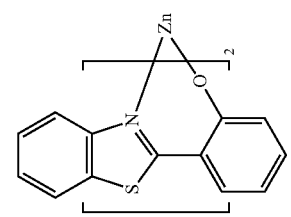 | Appl. Phys. Lett. 90, 123509 (2007) |
| Conjugated oligomers and polymers (e.g., polyfluorene) | 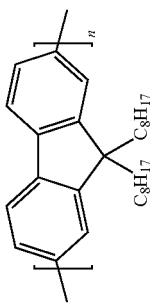 | Org. Electron. 1, 15 (2000) |
TABLE 1-continued TABLE 1-continued

| MATERIAL | EXAMPLES OF MATERIAL | PUBLICATIONS |
|---|---|---|
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |
| Arylcarbazoles | Green hosts | Appl. Phys. Lett. 78, 1622 (2001) |

TABLE 1-continued
| MATERIAL | EXAMPLES OF MATERIAL | PUBLICATIONS |
|---|---|---|
| | 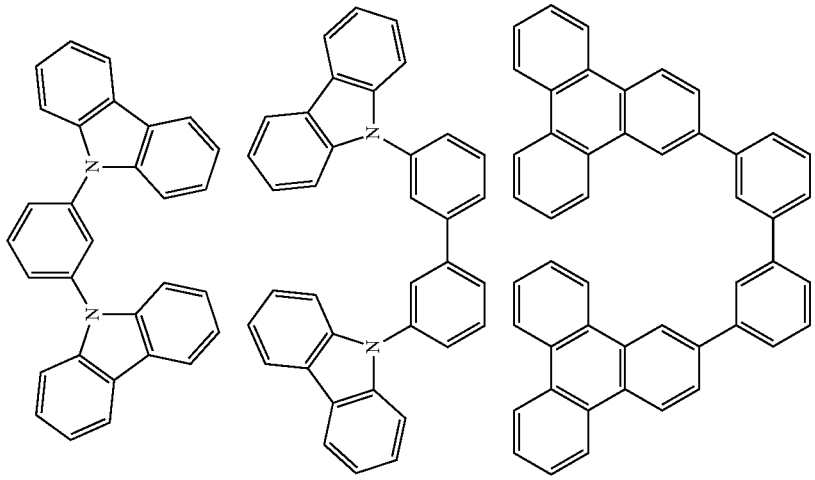 | US20030175553 |
| | | WO2001039234 |
| Aryltriphenylene compounds | 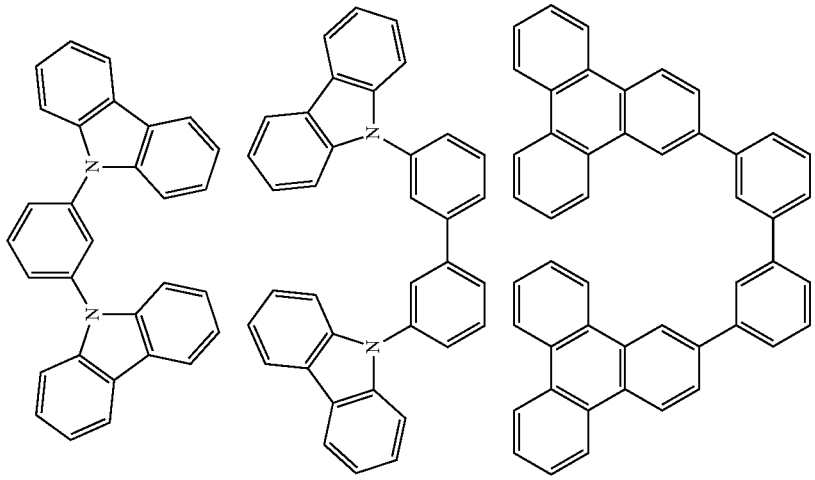 | US20060280965 |

TABLE 1-continued
| MATERIAL | EXAMPLES OF MATERIAL | PUBLICATIONS |
|---|---|---|
| | 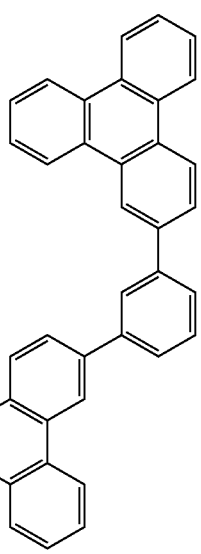 | US20060280965 |
| | 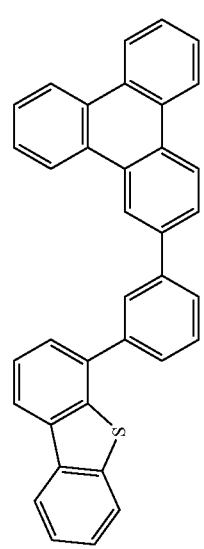 | WO2009021126 |
| Poly-fused heteroaryl compounds | 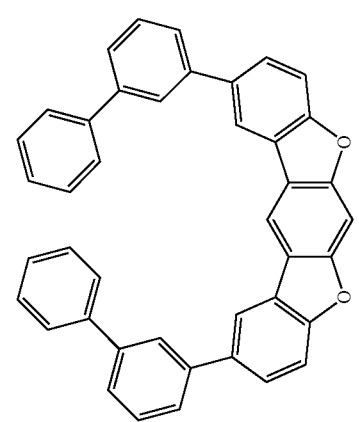 | US20090309488<br>US20090302743<br>US20100012931 |

TABLE 1-continued
| MATERIAL | EXAMPLES OF MATERIAL | PUBLICATIONS |
|---|---|---|
| Donor acceptor type molecules | 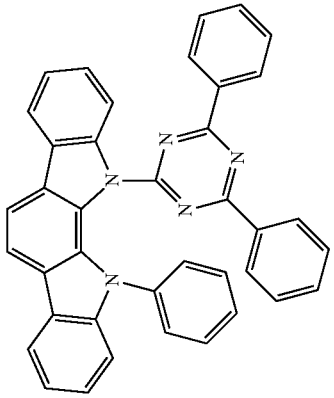 | WO2008056746 |
| | 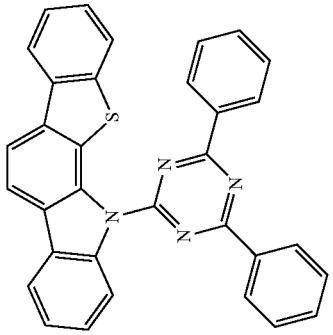 | WO2010107244 |

TABLE 1-continued
| MATERIAL | EXAMPLES OF MATERIAL | PUBLICATIONS |
|---|---|---|
| Aza-carbazole/DBT/DBF | 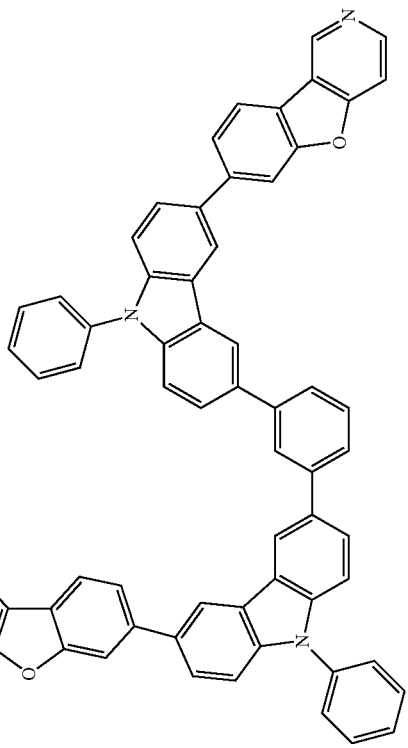 | JP2008074939 |
| | 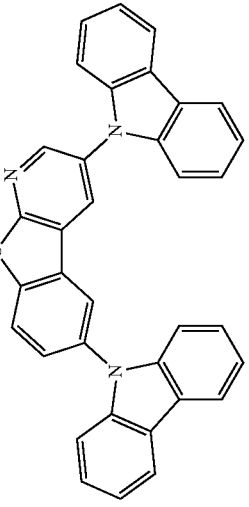 | US20100187984 |
| Polymers (e.g., PVK) | 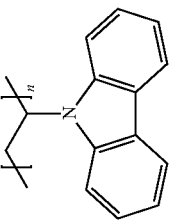 | Appl. Phys. Lett. 77, 2280 (2000) |

TABLE 1-continued
| MATERIAL | EXAMPLES OF MATERIAL | PUBLICATIONS |
|---|---|---|
| Spirofluorene compounds | 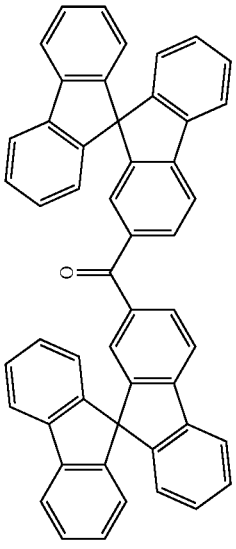 | WO2004093207 |
| Metal phenoxybenzooxazole compounds | 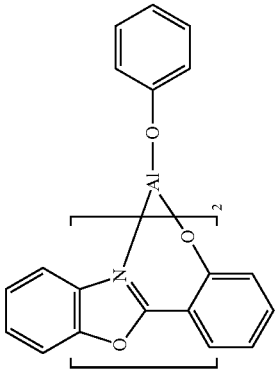 | WO2005089025<br>WO2006132173 |

TABLE 1-continued
| MATERIAL | EXAMPLES OF MATERIAL | PUBLICATIONS |
|---|---|---|
| | 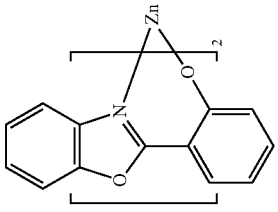 | JP2005111610 |
| | 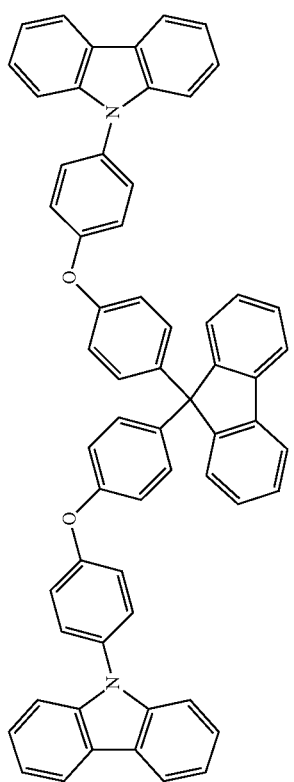 | JP2007254297 |
| Spirofluorene-carbazole compounds | 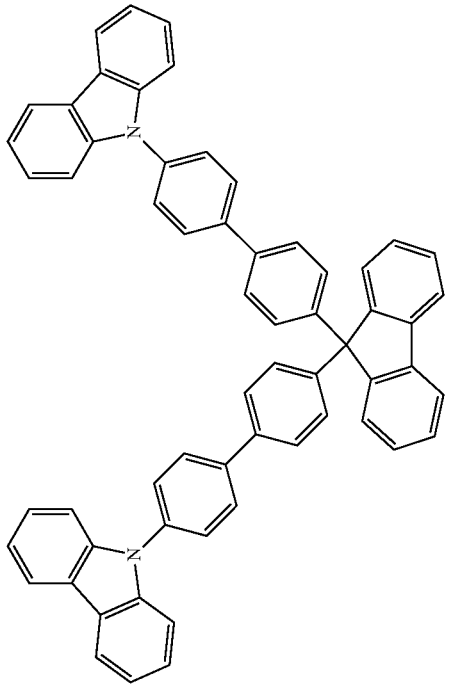 | JP2007254297 |

TABLE 1-continued
| MATERIAL | EXAMPLES OF MATERIAL | PUBLICATIONS |
|---|---|---|
| Indolocarbazoles | 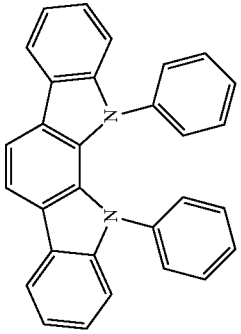 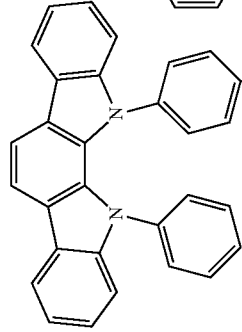 | WO2007063796 WO2007063754 |
| 5-member ring electron deficient heterocycles (e.g., triazole, oxadiazole) | 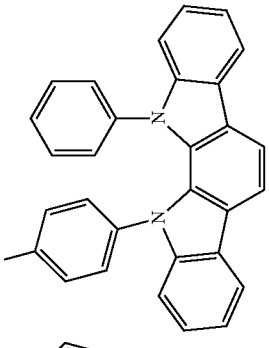 | J. Appl. Phys. 90, 5048 (2001) |

TABLE 1-continued
| MATERIAL | EXAMPLES OF MATERIAL | PUBLICATIONS |
|---|---|---|
| | 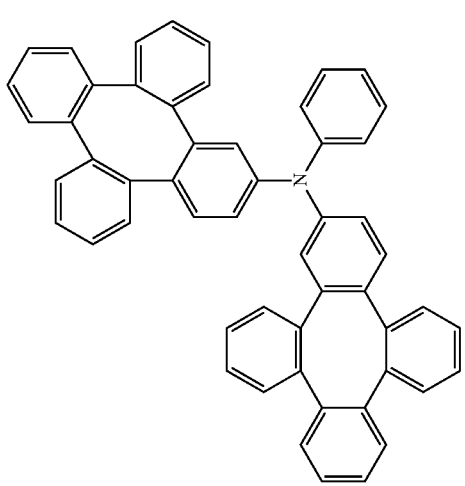 | WO2004107822 |
| Tetraphenylene complexes | 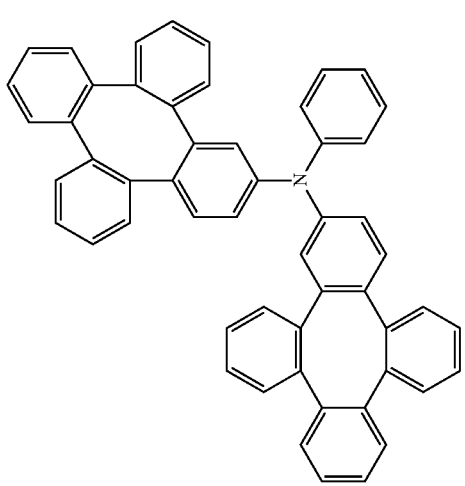 | US20050112407 |
| Metal phenoxypyridine compounds | 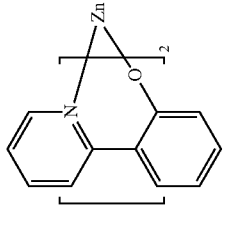 | WO2005030900 |

TABLE 1-continued
| MATERIAL | EXAMPLES OF MATERIAL | PUBLICATIONS |
|---|---|---|
| Metal coordination complexes (e.g., Zn, Al with N^N ligands) | 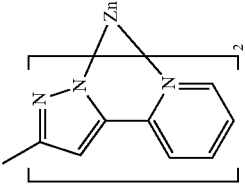 | US20040137268, US20040137267 |
| Blue hosts | | |
| Arylcarbazoles | 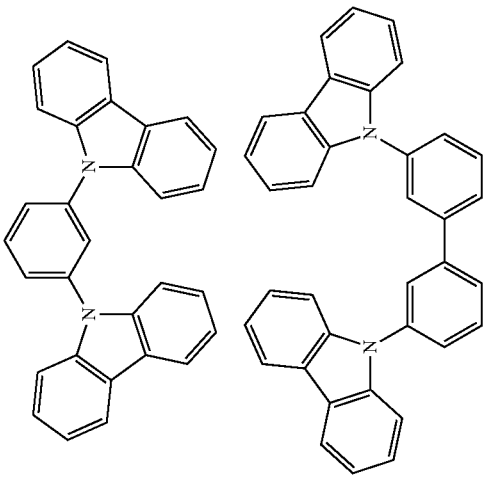 | Appl. Phys. Lett. 82, 2422 (2003) |
| | 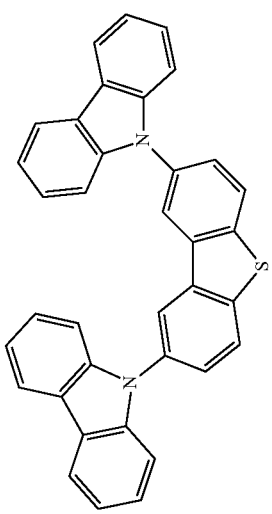 | US20070190359 |
| Dibenzothiophene/ Dibenzofuran-carbazole compounds | 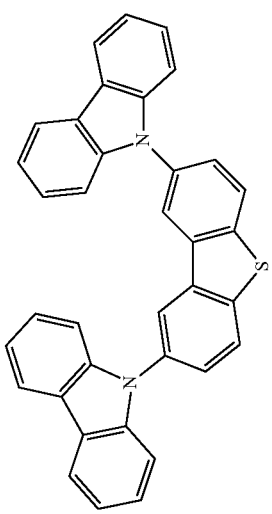 | WO2006114966, US20090167162 |

TABLE 1-continued
| MATERIAL | EXAMPLES OF MATERIAL | PUBLICATIONS |
|---|---|---|
| | 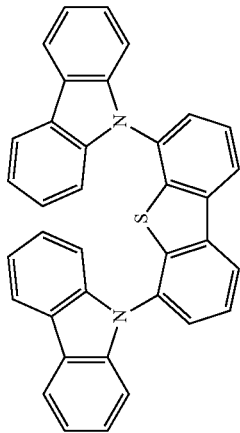 | US2009167162 |
| | 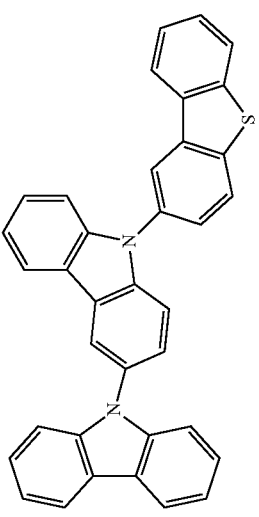 | WO2009086028 |
| | 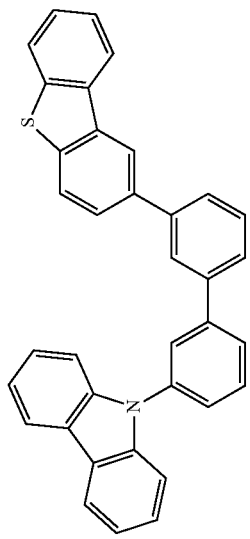 | US20090030202, US20090017330 |

TABLE 1-continued
| MATERIAL | EXAMPLES OF MATERIAL | PUBLICATIONS |
|---|---|---|
| | 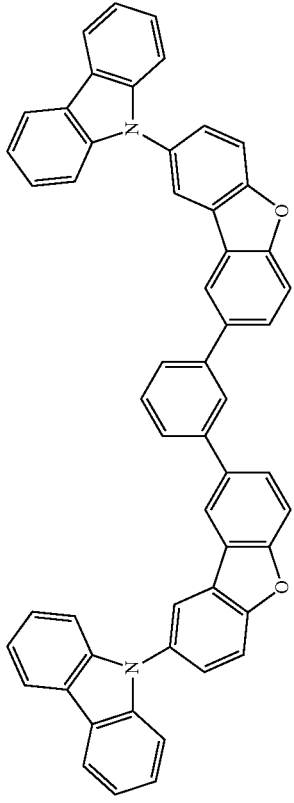 | US20100084966 |
| Silicon aryl compounds | 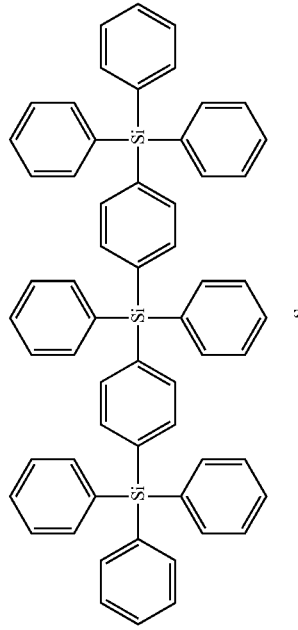 | US20050238919<br><br>WO2009003898 |

TABLE 1-continued

| MATERIAL | EXAMPLES OF MATERIAL | PUBLICATIONS |
|---|---|---|
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |

TABLE 1-continued

| MATERIAL | EXAMPLES OF MATERIAL | PUBLICATIONS |
|---|---|---|
| High triplet metal organometallic complex | | U.S. Pat No. 7,154,114 |
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |

TABLE 1-continued

| MATERIAL | EXAMPLES OF MATERIAL | PUBLICATIONS |
|---|---|---|
| | | US20030072964 |
| | | US20030072964 |
| | | US20060202194 |

TABLE 1-continued

| MATERIAL | EXAMPLES OF MATERIAL | PUBLICATIONS |
|---|---|---|
| | | US20060202194 |
| | | US20070087321 |
| | | US20080261076
US20100090591 |

TABLE 1-continued
| MATERIAL | EXAMPLES OF MATERIAL | PUBLICATIONS |
|---|---|---|
| | 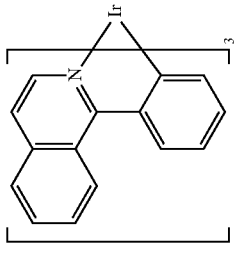 | US20070087321<br><br>Adv. Mater. 19, 739 (2007) |
| | 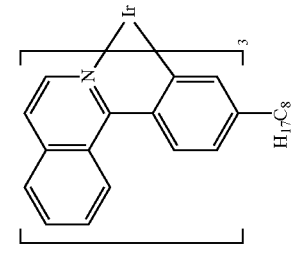 | WO2009100991 |

TABLE 1-continued
| MATERIAL | EXAMPLES OF MATERIAL | PUBLICATIONS |
|---|---|---|
| | 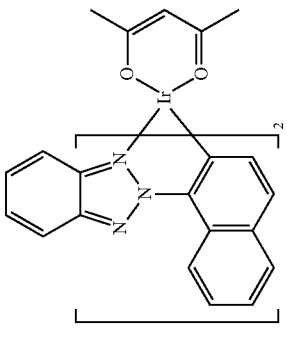 | WO2008101842 |
| | 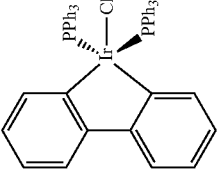 | U.S. Pat. No. 7,232,618 |
| Platinum(II) organometallic complexes | 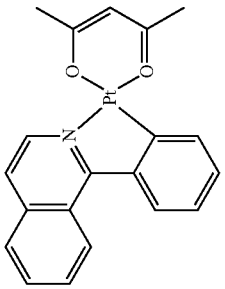 | WO2003040257 |

TABLE 1-continued
| MATERIAL | EXAMPLES OF MATERIAL | PUBLICATIONS |
|---|---|---|
| | 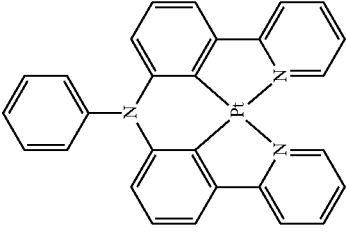 | US20070103060 |
| Osminum(III) complexes | 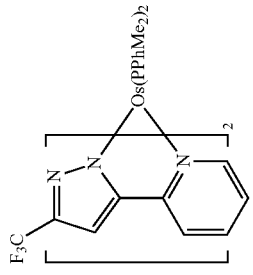 | Chem. Mater. 17, 3532 (2005) |
| Ruthenium(II) complexes | | Adv. Mater. 17, 1059 (2005) |
| Rhenium (I), (II), and (III) complexes | 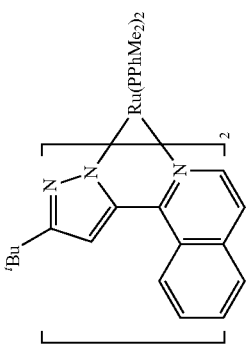 | US20050244673 |

TABLE 1-continued
| MATERIAL | EXAMPLES OF MATERIAL | PUBLICATIONS |
|---|---|---|
| | Green dopants | |
| Iridium(III) organometallic complexes | 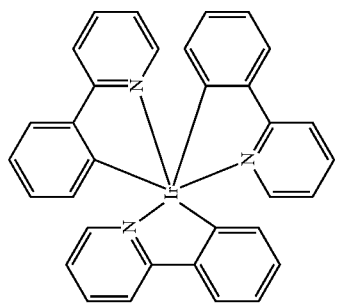 | Inorg. Chem. 40, 1704 (2001) |
| | 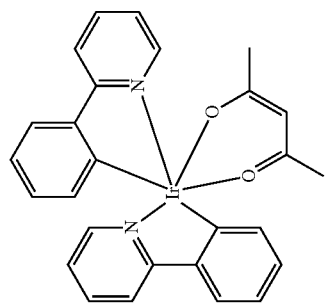 and its derivatives | US20020034656 |

TABLE 1-continued
| MATERIAL | EXAMPLES OF MATERIAL | PUBLICATIONS |
|---|---|---|
| | 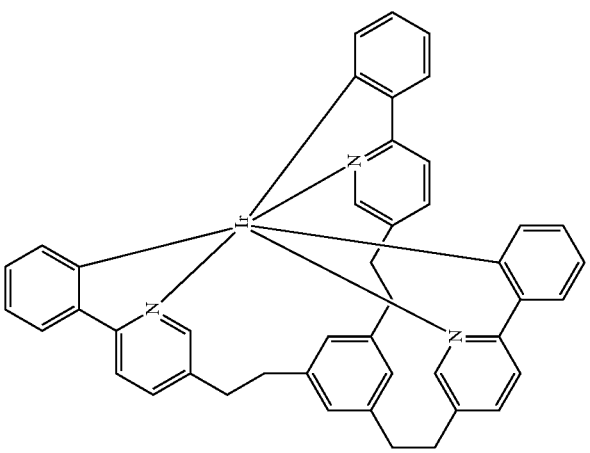 | U.S. Pat. No. 7,332,232 |
| | 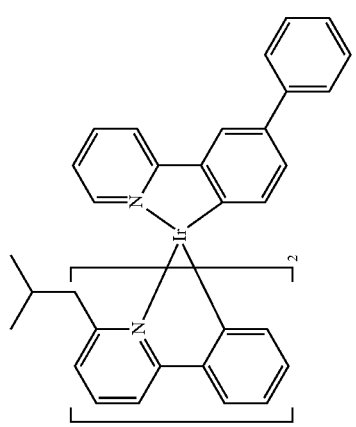 | US20090108737 |

TABLE 1-continued
| MATERIAL | EXAMPLES OF MATERIAL | PUBLICATIONS |
|---|---|---|
| | 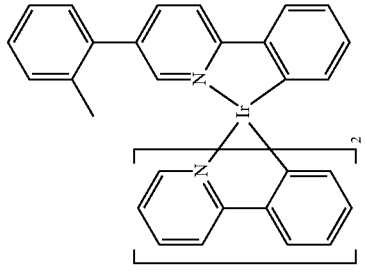 | WO2010028151 |
| | 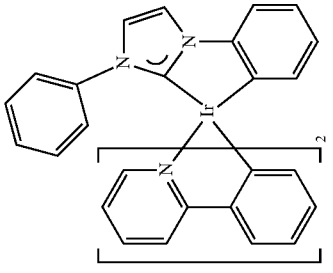 | EP1841834B |
| | 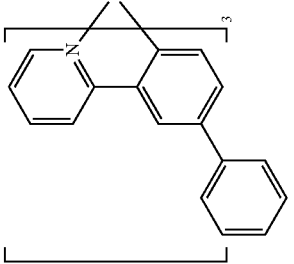 | US20060127696 |

TABLE 1-continued
| MATERIAL | EXAMPLES OF MATERIAL | PUBLICATIONS |
|---|---|---|
| | 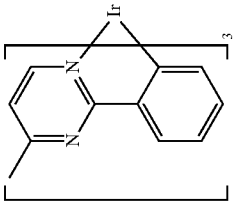 | US20090039776 |
| | 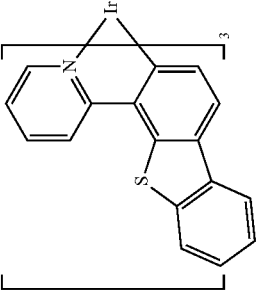 | U.S. Pat. No. 6,921,915 |
| | 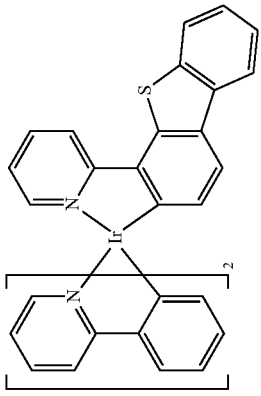 | US2010244004 |

TABLE 1-continued

| MATERIAL | EXAMPLES OF MATERIAL | PUBLICATIONS |
|---|---|---|
| | (structure) | U.S. Pat. No. 6,687,266 |
| | (structure) | Chem. Mater. 16, 2480 (2004) |
| | (structure) | US20070190359 |

TABLE 1-continued
| MATERIAL | EXAMPLES OF MATERIAL | PUBLICATIONS |
|---|---|---|
| | 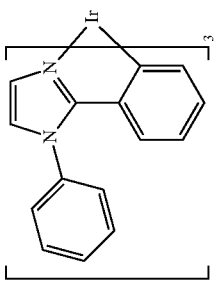 | US20060008670 JP2007123392 |
| | | WO2010086089, WO2011044988 |
| | | Adv. Mater. 16, 2003 (2004) |
| | 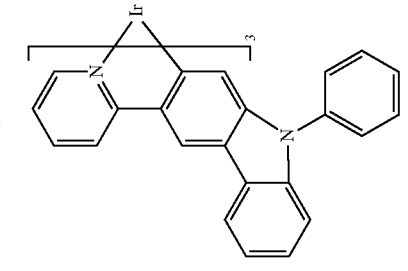 | Angew. Chem. Int. Ed. 2006, 45, 7800 |

TABLE 1-continued

| MATERIAL | EXAMPLES OF MATERIAL | PUBLICATIONS |
|---|---|---|
| | | WO2009050290 |
| | | US20090165846 |
| | | US20080015355 |
| | | US20010015432 |

TABLE 1-continued
| MATERIAL | EXAMPLES OF MATERIAL | PUBLICATIONS |
|---|---|---|
| Monomer for polymeric metal organometallic compounds | 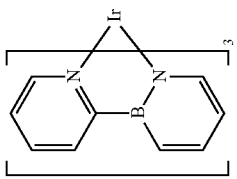 | US20100295032 |
| | 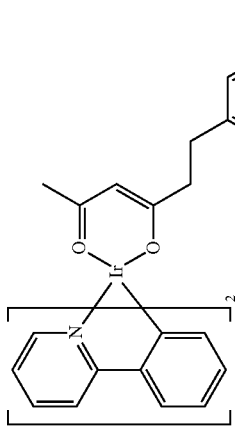 | U.S. Pat. No. 7,250,226, U.S. Pat. No. 7,396,598 |
| Pt(II) organometallic complexes, including polydentated ligands | 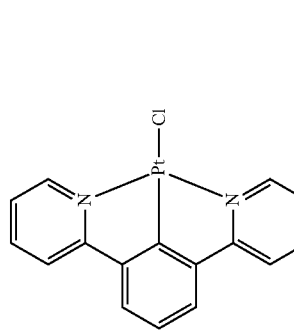 | Appl. Phys. Lett. 86, 153505 (2005) |

TABLE 1-continued
| MATERIAL | EXAMPLES OF MATERIAL | PUBLICATIONS |
|---|---|---|
| | 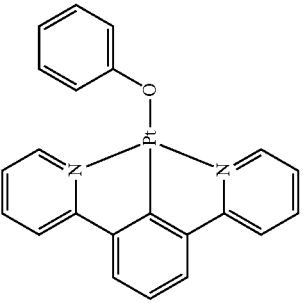 | Appl. Phys. Lett. 86, 153505 (2005)<br><br>Chem. Lett. 34, 592 (2005)<br><br>WO2002015645 |

TABLE 1-continued
| MATERIAL | EXAMPLES OF MATERIAL | PUBLICATIONS |
|---|---|---|
| | 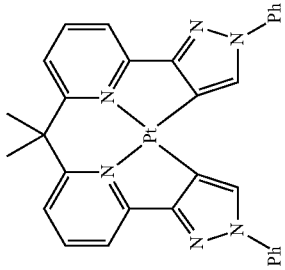 | US20060263635<br><br>US20060182992<br>US20070103060<br><br>WO2009000673 |
| Cu complexes | | |

TABLE 1-continued
| MATERIAL | EXAMPLES OF MATERIAL | PUBLICATIONS |
|---|---|---|
| | 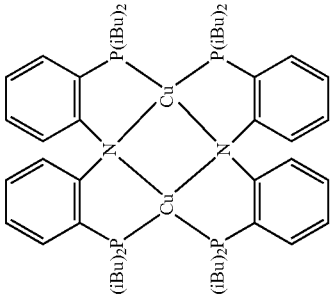 | US20070111026 |
| Gold complexes | 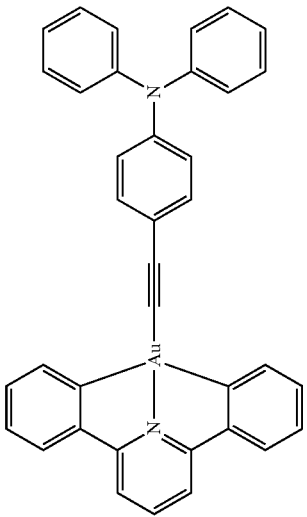 | Chem. Commun. 2906 (2005) |
| Rhenium(III) complexes | 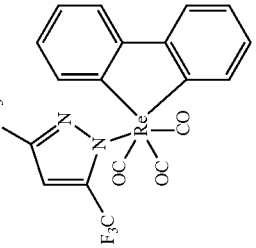 | Inorg. Chem. 42, 1248 (2003) |

TABLE 1-continued
| MATERIAL | EXAMPLES OF MATERIAL | PUBLICATIONS |
|---|---|---|
| Osmium(II) complexes | 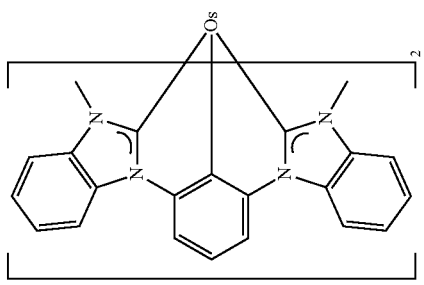 | U.S. Pat. No. 7,279,704 |
| Deuterated organometallic complexes | | US2003138657 |

TABLE 1-continued
| MATERIAL | EXAMPLES OF MATERIAL | PUBLICATIONS |
|---|---|---|
| Organometallic complexes with two or more metal centers | 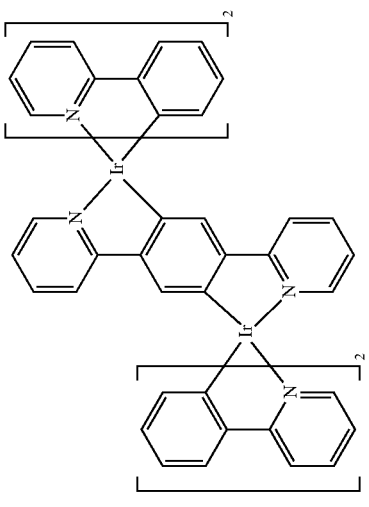 | US20030152802 |
| | 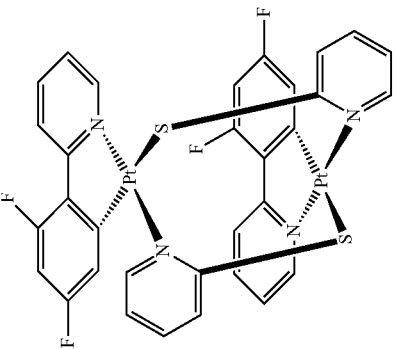 | U.S. Pat. No. 7,090,928 |

TABLE 1-continued
| MATERIAL | EXAMPLES OF MATERIAL | PUBLICATIONS |
|---|---|---|
| | Blue dopants | |
| Iridium(III) organometallic complexes | 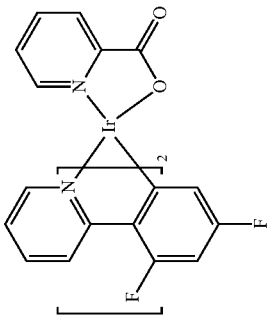 | WO2002002714 |
| | 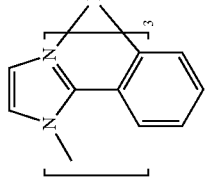 | WO2006009024 |
| | 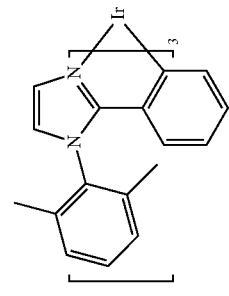 | US20060251923<br>US20110057559<br>US20110204333 |
| | 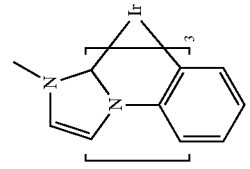 | U.S. Pat. No. 7,393,599,<br>WO2006005418,<br>US20050260441,<br>WO2005019373 |

TABLE 1-continued

| MATERIAL | EXAMPLES OF MATERIAL | PUBLICATIONS |
|---|---|---|
| | | U.S. Pat. No. 7,534,505 |
| | | WO2011051404 |
| | | U.S. Pat. No. 7,445,855 |

TABLE 1-continued
| MATERIAL | EXAMPLES OF MATERIAL | PUBLICATIONS |
|---|---|---|
| | 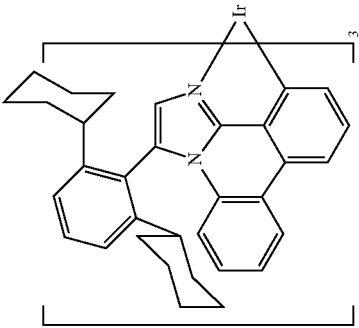 | US20070190359, US20080297033 US20100148663 |
| | 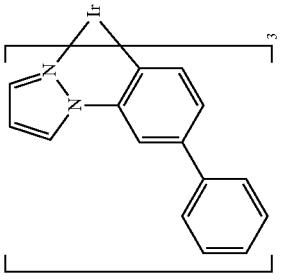 | U.S. Pat. No. 7,338,722 |
| | 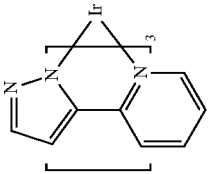 | US20020134984 |

TABLE 1-continued
| MATERIAL | EXAMPLES OF MATERIAL | PUBLICATIONS |
|---|---|---|
| | 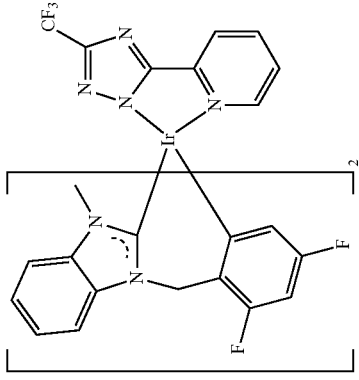 | Angew. Chem. Int. Ed. 47, 4542 (2008) |
| | 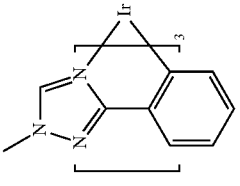 | Chem. Mater. 18, 5119 (2006) |
| | 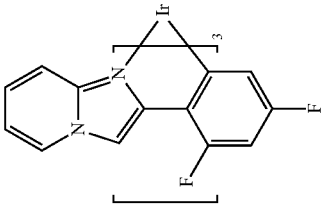 | Inorg. Chem. 46, 4308 (2007) |

TABLE 1-continued
| MATERIAL | EXAMPLES OF MATERIAL | PUBLICATIONS |
|---|---|---|
| | 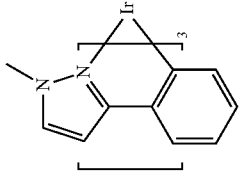 | WO2005123873 |
| | 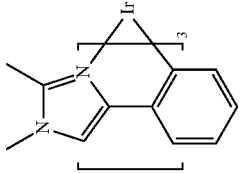 | WO2005123873 |
| | 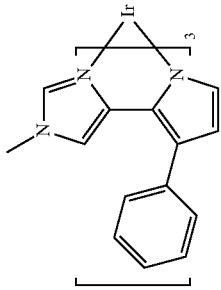 | WO2007004380 |

TABLE 1-continued
| MATERIAL | EXAMPLES OF MATERIAL | PUBLICATIONS |
|---|---|---|
| | 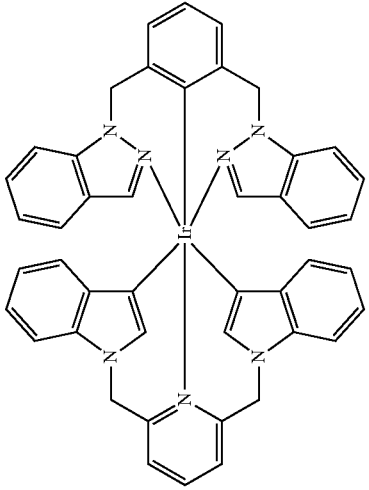 | WO2006082742<br><br>U.S. Pat. No. 7,279,704<br><br>Organometallics 23, 3745 (2004) |
| Osmium(II) complexes | | |

TABLE 1-continued
| MATERIAL | EXAMPLES OF MATERIAL | PUBLICATIONS |
|---|---|---|
| Gold complexes | 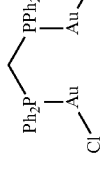 | Appl. Phys. Lett. 74, 1361 (1999) |
| Platinum(II) complexes | 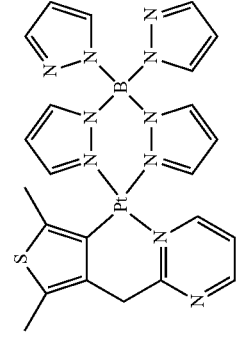 | WO2006098120, WO2006103874 |
| Pt tetradentate complexes with at least one metal-carbene bond | 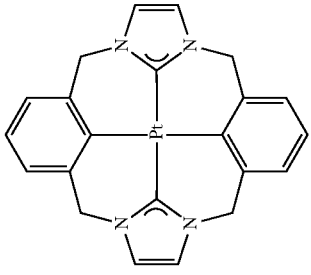 | U.S. Pat. No. 7,655,323 |
| Exciton/hole blocking layer materials | | |
| Bathocuprine compounds (e.g. BCP, BPhen) | 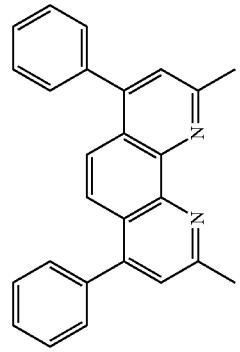 | Appl. Phys. Lett. 75, 4 (1999) |

TABLE 1-continued
| MATERIAL | EXAMPLES OF MATERIAL | PUBLICATIONS |
|---|---|---|
| | | Appl. Phys. Lett. 79, 449 (2001) |
| Metal 8-hydroxyquinolates (e.g., BAlq) | 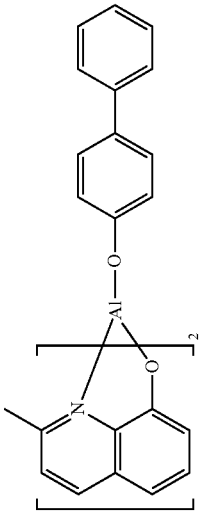 | Appl. Phys. Lett. 81, 162 (2002) |
| 5-member ring electron deficient heterocycles such as triazole, oxadiazole, imidazole, benzoimidazole | 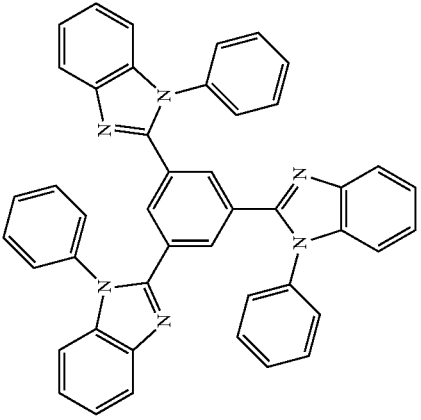 | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 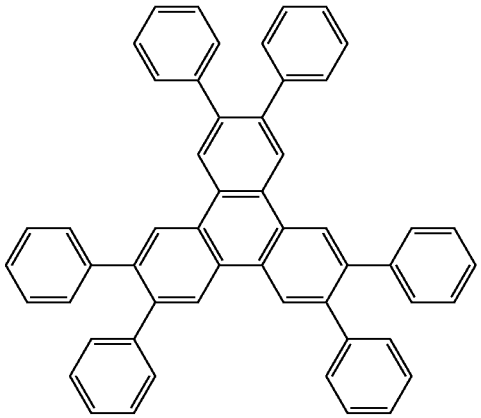 | US20050025993 |

TABLE 1-continued
| MATERIAL | EXAMPLES OF MATERIAL | PUBLICATIONS |
|---|---|---|
| Fluorinated aromatic compounds | 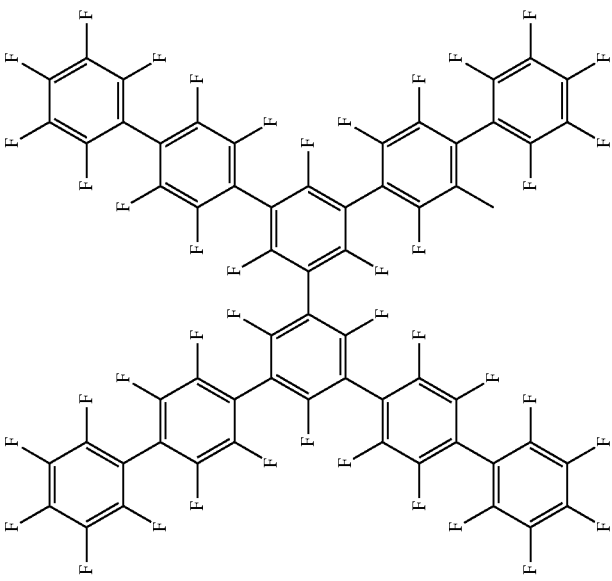 | Appl. Phys. Lett. 79, 156 (2001) |
| Phenothiazine-S-oxide | 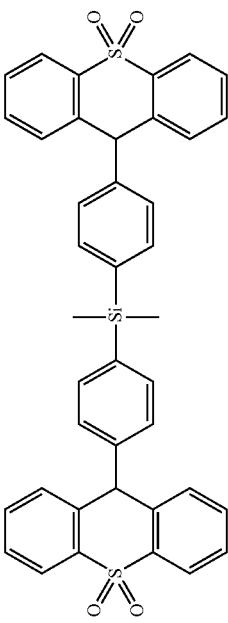 | WO2008132085 |

TABLE 1-continued
| MATERIAL | EXAMPLES OF MATERIAL | PUBLICATIONS |
|---|---|---|
| Silylated five-membered nitrogen, oxygen, sulfur or phosphorus dibenzoheterocycles | 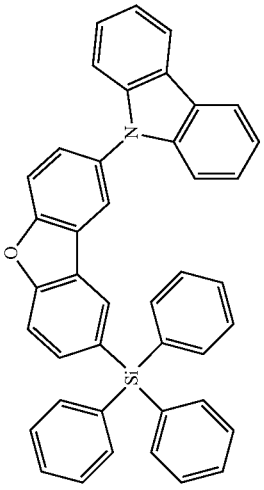 | WO2010079051 |
| Aza-carbazoles | 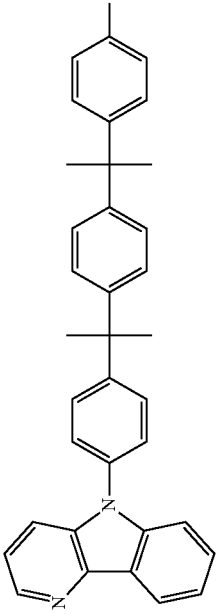 | US20060121308 |
| | Electron transporting materials | |
| Anthracene-benzoimidazole compounds | 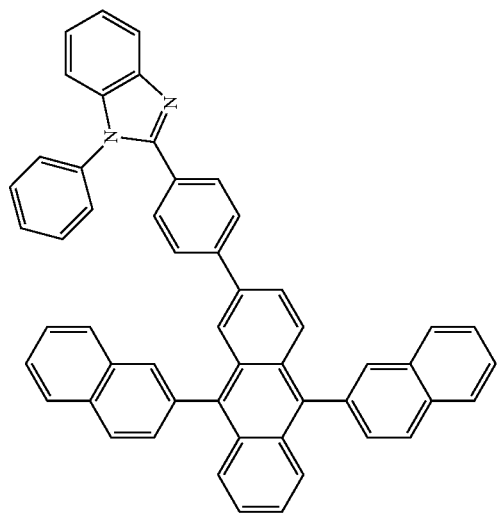 | WO2003060956 |

TABLE 1-continued
| MATERIAL | EXAMPLES OF MATERIAL | PUBLICATIONS |
|---|---|---|
| Aza triphenylene derivatives | 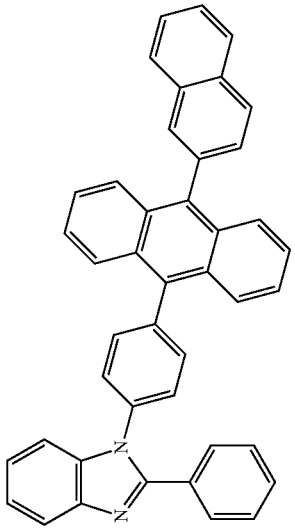 | US20090179554 |
| | 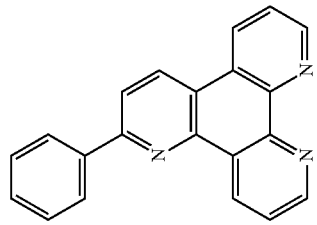 | US20090115316 |
| Anthracene-benzothiazole compounds | 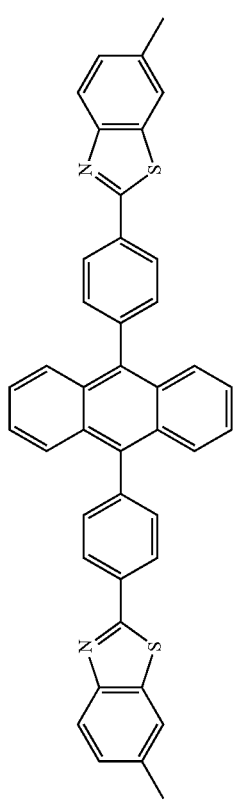 | Appl. Phys. Lett. 89, 063504 (2006) |
| Metal 8-hydroxyquinolates (e.g. Alq$_3$, Zrq$_4$) | 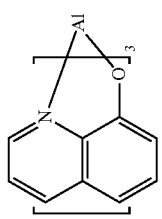 | Appl. Phys. Lett. 51, 913 (1987) U.S. Pat. No. 7,230,107 |

TABLE 1-continued
| MATERIAL | EXAMPLES OF MATERIAL | PUBLICATIONS |
|---|---|---|
| Metal hydroxybenoquinolates | 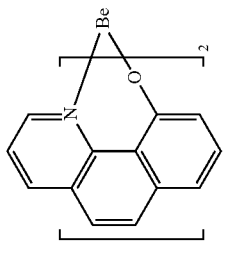 | Chem. Lett. 5, 905 (1993) |
| Bathocuprine compounds such as BCP, BPhen, etc | 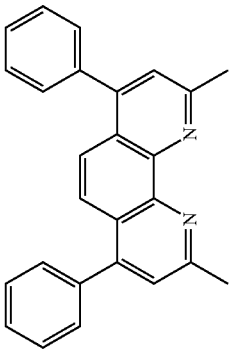 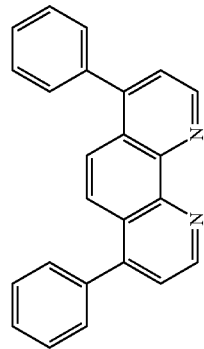 | Appl. Phys. Lett. 91, 263503 (2007)<br><br>Appl. Phys. Lett. 79, 449 (2001) |

TABLE 1-continued
| MATERIAL | EXAMPLES OF MATERIAL | PUBLICATIONS |
|---|---|---|
| 5-member ring electron deficient heterocycles (e.g. triazole, oxadiazole, imidazole, benzoimidazole) | 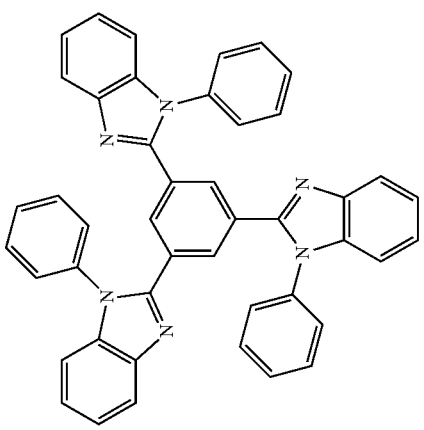 | Appl. Phys. Lett. 74, 865 (1999)<br><br>Appl. Phys. Lett. 55, 1489 (1989)<br><br>Jpn. J. Apply. Phys. 32, L917 (1993) |
| Silole compounds | 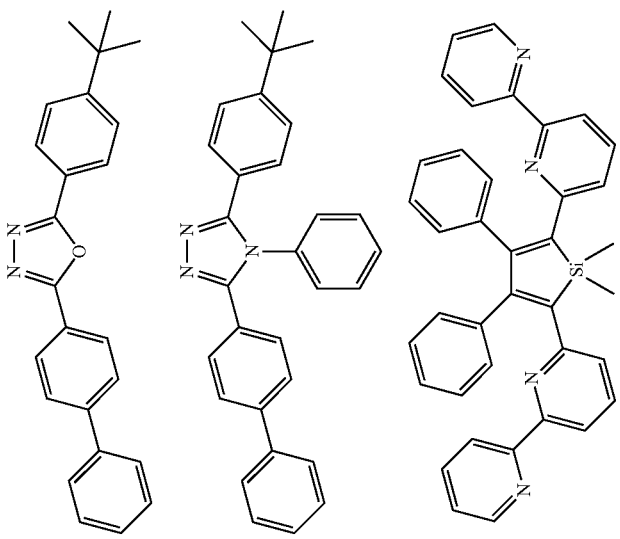 | Org. Electron. 4, 113 (2003) |

TABLE 1-continued

| MATERIAL | EXAMPLES OF MATERIAL | PUBLICATIONS |
|---|---|---|
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |

TABLE 1-continued
| MATERIAL | EXAMPLES OF MATERIAL | PUBLICATIONS |
|---|---|---|
| Triazine complexes | 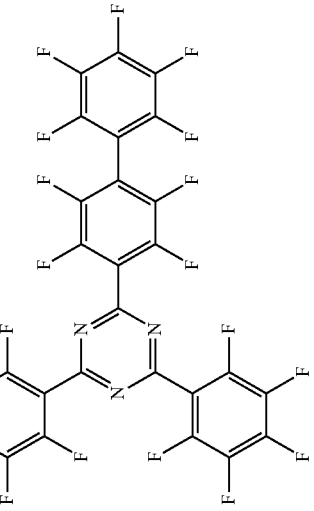 | US20040036077 |
| Zn (N^N) complexes | 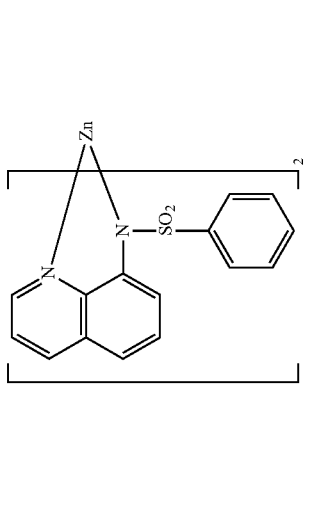 | U.S. Pat. No. 6,528,187 |

Modeling

Non-limiting examples consistent with the embodiments described above will now be discussed. These examples are for experimental purposes only and are in no way limiting to the scope of this work.

Model Device 1 and Comparative Examples: B1 as the Deep Homo Emitter

Model Device 1 has a similar structure to OLED 300 as shown in FIG. 3.

In this Model Device 1, HAT-CN is used as the hole insertion layer. The thickness of the layer is 100 Å. NPD is used as the hole transporting layer with a thickness of 300 Å. Alq3 is used as the electron transport layer with a thickness of 400 Å. LiF is used as the electron insertion layer with a thickness of 10 Å. The chemical structures for NPD, HAT-CH, and Alq$_3$ are shown below:

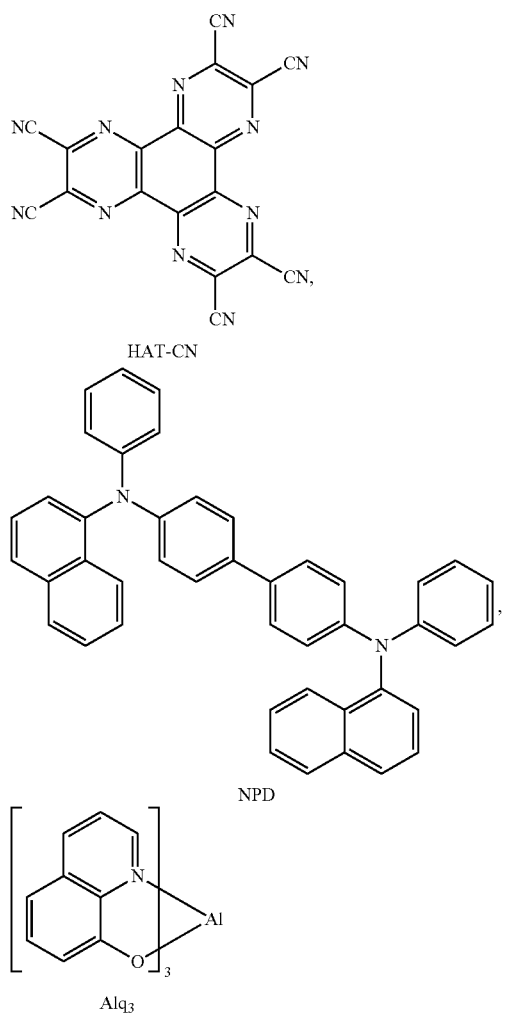

H1 is used as the electron blocking layer to block electrons and exciton leakage into the hole transporting layer. It has a thickness of 50 Å. E1 is used as the hole blocking layer to block holes and exciton leakage into the electron transporting layer. It has a thickness of 50 Å. The organic emissive layer of Model Device 1 has four components: E1, H1, M2 and B1. E1 is the electron transporting compound. H1 is the hole transporting compound. M2 is the wide band gap host-matrix. B1 is the emitting compound. Its combined thickness is 300 Å. The chemical structure for these molecules are shown below:

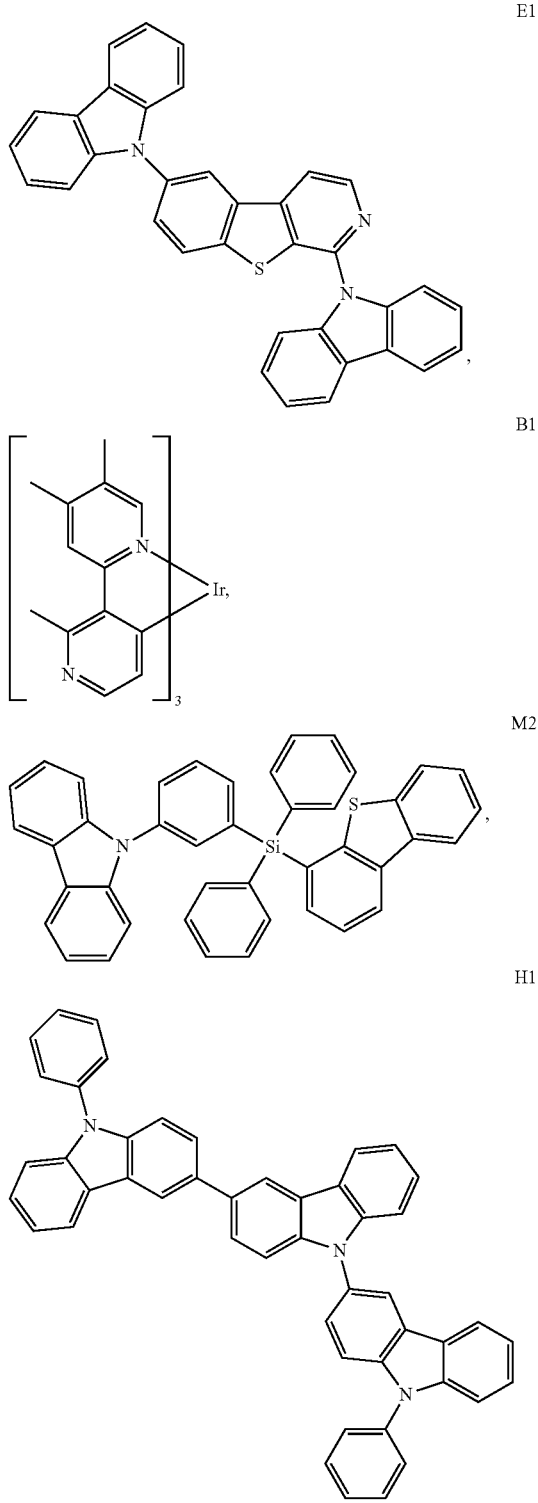

Table 2 shows the T1, HOMO, and LUMO energy levels of these compounds. The energy levels described here were experimentally determined through methods described above.

TABLE 2

Energy Levels of compounds used in Model Devices.

| Compound | HOMO [eV] | LUMO [eV] | T1 [eV] |
|---|---|---|---|
| M1 | 5.96 | 2.16 | 2.64 |
| M2 | 5.68 | 1.99 | 3.04 |
| E1 | 5.70 | 2.47 | 3.04 |
| H1 | 5.38 | 1.84 | 2.73 |
| B1 | 5.45 | 2.14 | 2.62 |
| B2 | 5.58 | 2.29 | 2.74 |
| G1 | 5.23 | 2.07 | 2.43 |
| Ir(ppy) | 5.11 | 2.10 | 2.61 |

Seven devices were also constructed as a way of comparative examples to Model Device 1. All seven are similar in structure and design as Model Device 1 except that they are lack one or a combination of these four components: an electron transporting compound in the organic emissive layer, a hole blocking compound in the organic emissive layer, an electron blocking layer, and a hole blocking layer. Additionally, some of the comparative examples use a different host material than Model Device 1. Table 3A details the structural differences between the seven comparative devices and the Model Device 1. Table 3B details the output of the devices, such as voltage, luminous efficacy, EQE, power efficacy and relative lifetime.

TABLE 3A

Experimental Data for Model Device 1 and Comparative Examples

B1 blue Emitter

| Example | EBL [Å] | Host | Electron transporting compound | Hole transporting compound | B1 [%] | HBL [Å] | 1931 CIE x | 1931 CIE y |
|---|---|---|---|---|---|---|---|---|
| CE1 | H1 50Å | M2 | — | — | 5 | E1 50Å | 0.172 | 0.374 |
| CE2 | H1 50Å | M2 | — | H1 15% | 5 | E1 50Å | 0.166 | 0.367 |
| CE3 | H1 50Å | E1 | — | — | 5 | E1 50Å | 0.181 | 0.416 |
| CE4 | H1 50Å | E1 | — | H1 15% | 5 | E1 50Å | 0.179 | 0.413 |
| CE5 | — | M2 | E1 25% | H1 15% | 5 | — | 0.177 | 0.373 |
| CE6 | — | M2 | E1 25% | H1 15% | 5 | E1 50Å | 0.167 | 0.370 |
| CE7 | H1 50Å | M2 | E1 25% | H1 15% | 5 | — | 0.181 | 0.387 |
| Model Device 1 | H1 50Å | M2 | E1 25% | H1 15% | 5 | E1 50Å | 0.169 | 0.383 |

TABLE 3B

Experimental Data for Model Device 1 and Comparative Examples

At 1,000 nits

| Example | λ max [nm] | FWHM [nm] | Voltage [V] | Relative LE [%] | Relative EQE [%] | Relative LT [%] |
|---|---|---|---|---|---|---|
| CE1 | 472 | 64 | 6.8 | 37 | 37 | 7 |
| CE2 | 472 | 60 | 5.2 | 59 | 61 | 17 |
| CE3 | 500 | 70 | 6.1 | 30 | 28 | 11 |
| CE4 | 500 | 70 | 4.7 | 74 | 70 | 50 |
| CE5 | 472 | 62 | 5.6 | 31 | 31 | 45 |
| CE6 | 472 | 60 | 5.0 | 76 | 77 | 69 |
| CE7 | 474 | 66 | 5.3 | 33 | 32 | 62 |
| Model Device 1 | 474 | 64 | 4.6 | 100 | 100 | 100 |

Figure 4:
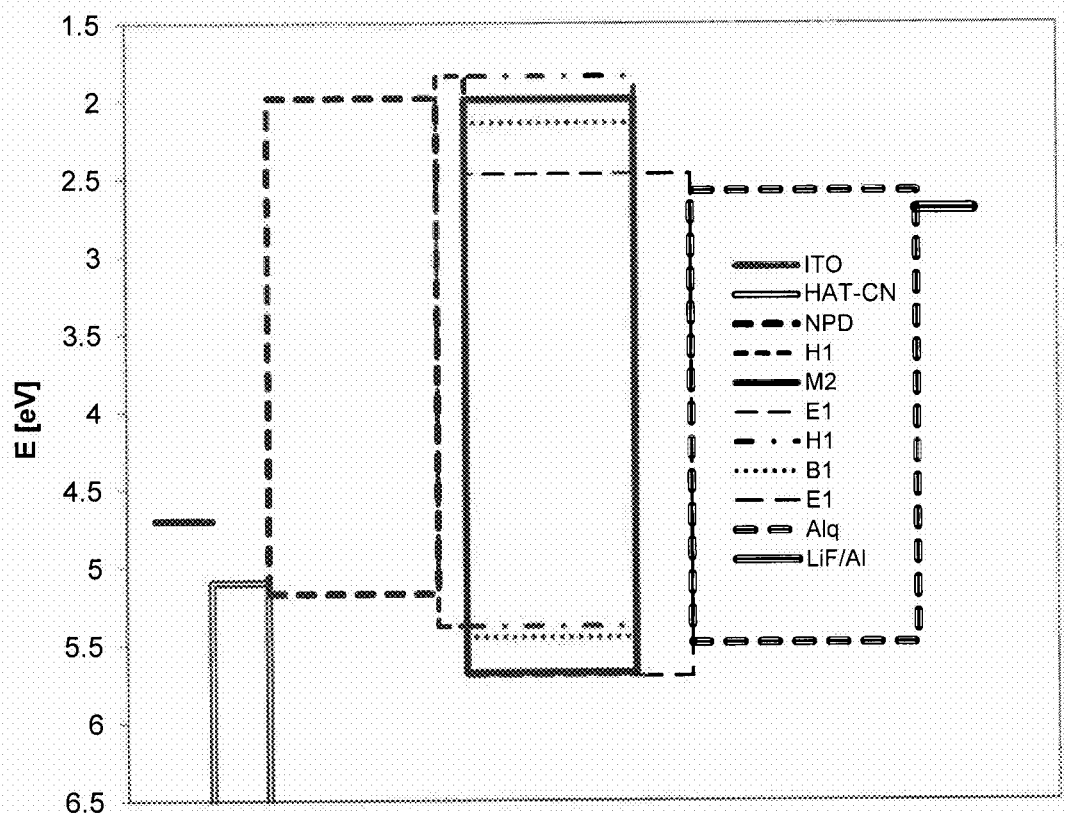
FIG. 4 shows the energy level diagram for an OLED using B1 as an emitting compound.

As can be seen in Table 3, Model Device 1 has the highest relative EQE, the lowest voltage, highest power efficacy, and the longest lifetime as compared to all the comparative devices. FIG. 4 depicts the energy level diagram for Model Device 1.

CE1 lacks an electron transporting compound and a hole transporting compound in its organic emissive layer. The relative EQE of CE1 is only 37% (at 1,000 nits). It only has a 7% relative lifetime compared to Model Device 1. CE1 also has a high voltage, indicating that there is not sufficient charge transport and recombination of electrons and holes in the organic emissive layer.

CE2 lacks an electron transporting compound in its organic emissive layer. The relative EQE of this device is only 61%. It has only a 17% relative lifetime compared to Model Device 1. The decreased performance of this device is due to the lack of proper electron transport in the organic emissive layer.

CE3 lacks both an electron transporting compound and a hole transporting compound in its organic emissive layer. It is also different from Model Device 1 because it uses E1 as its host compound in the organic emissive layer. Its relative EQE is only 28%. It has a relative lifetime of only 11% compared to Model Device 1. This is because CE3 does not provide enough charge transport in the organic emissive layer.

CE4 lacks an electron transporting compound in its organic emissive layer. It is also different from Model Device 1 because it uses E1 as its host compound. The relative EQE of this device is 70%. The relative lifetime is only 50% of the lifetime of Model Device 1.

CE5 lacks an electron blocking layer and a hole blocking layer. The relative EQE of this device is only 31%. Its relative lifetime is only 45% of the lifetime of Model Device 1. In this device, both holes and electrons can leak from the organic emissive layer without recombination. Excitons can leak as well.

CE6 lacks an electron blocking layer. Without an electron blocking layer, electrons and excitons can leak into the hole transport layer. The relative EQE of this device is 77%. Its relative lifetime as compared to the Model Device 1 is 69%.

CE7 lacks a hole blocking layer. The relative EQE of this device is 32%. It has a relative lifetime of 62% compared to the lifetime of Model Device 1. In this device, holes and excitons can leak into the electron transport layer.

Model Device 2 and Comparative Examples: B2 as the Deep Homo Emitter

Model Device 2 has a similar structure to Model Device 1 and OLED 300 as shown in FIG. 3. It is different in that the deep HOMO emitter is B2. E2's chemical structure is shown below:

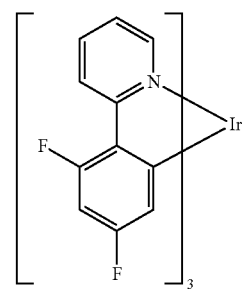

B2

Figure 5:
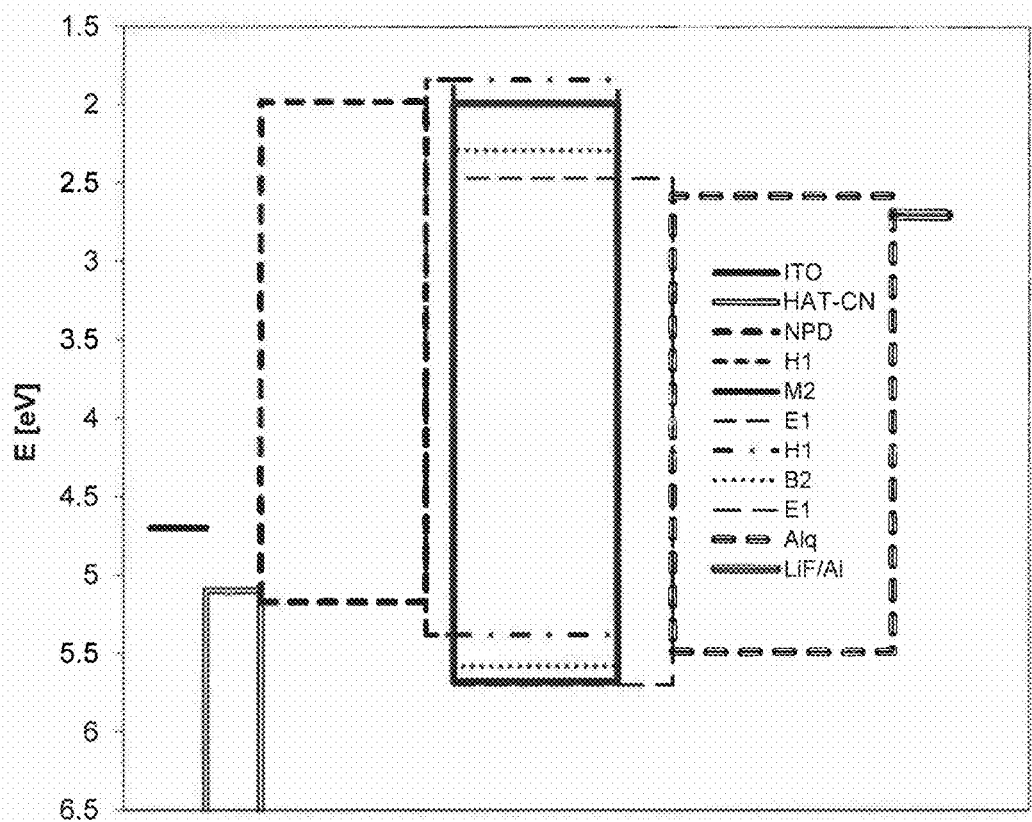
FIG. 5 shows the energy level diagram for an OLED using B2 as an emitting compound.

Table 1 shows the T1, HOMO, and LUMO energy levels of B2. Additionally, FIG. 5 depicts the energy level diagram of Model Device 2.

Three devices were constructed as a way of comparative examples to Model Device 2. These comparative devices are different from Model Device 2 because they each lack different components and/or use a different host material. Table 4A details the difference between these three comparative examples and Model Device 2. Table 4B details the output of Model Device 2 and the comparative examples.

TABLE 4A

Experimental Data for Model Device 2 and Comparative Examples

B2 blue Emitter

| Example | EBL [Å] | Host | Electron transporting compound | Hole transporting compound | B2 [%] | 1931 CIE x | 1931 CIE y |
|---|---|---|---|---|---|---|---|
| CE 8 | H1 50 Å | H1 | — | — | 5 | 0.155 | 0.331 |
| CE 9 | H1 50 Å | M2 | E1 25% | — | 5 | 0.180 | 0.377 |
| CE 10 | — | M2 | E1 25% | — | 5 | 0.174 | 0.257 |
| Model Device 2 | H1 50 Å | M2 | E1 25% | H1 30% | 5 | 0.156 | 0.330 |

TABLE 4B

Experimental Data for Model Device 2 and Comparative Examples

|  |  |  | At 1,000 nits | | | |
|---|---|---|---|---|---|---|
| Example | λ max [nm] | FWHM [nm] | Voltage [V] | Relative LE [%] | Relative EQE [%] | Relative LT [%] |
| CE 8 | 472 | 58 | 5.7 | 45 | 45 | 24 |
| CE 9 | 472 | 72 | 7.9 | 47 | 42 | 31 |
| CE 10 | 470 | 74 | 10.2 | 12 | 13 | 12 |
| Model Device 2 | 470 | 58 | 5.6 | 100 | 100 | 100 |

CE8 lacks an electron transporting compound in its organic emissive layer. It is also different from Model Device 2 in that it uses H1 as a host material and not M2. As can be seen from Table 4, its relative EQE is 45%. Its relative lifetime compared to Model Device 2 is 24%.

CE9 lacks a hole transporting compound in its organic emissive layer. Its relative EQE is 42%. Its relative lifetime compared to Model Device 2 is 31%.

CEC10 lacks a hole transporting compound in its organic emissive layer. It also lacks an electron blocking layer. Its relative EQE is 13% and its relative lifetime is 12% as compared to Model Device 2.

Model Device 3 and Comparative Examples: G1 as the Deep Homo Emitter

Model Device 3 has a similar structure to OLED 300 as shown in FIG. 3 and Model Devices 1 and 2. It is different in that the deep HOMO emitter is G1 and the host material is M1. Also, the layer of its NPD is 450 Å instead of 300 Å. The chemical structures of G1 and M1 are shown below:

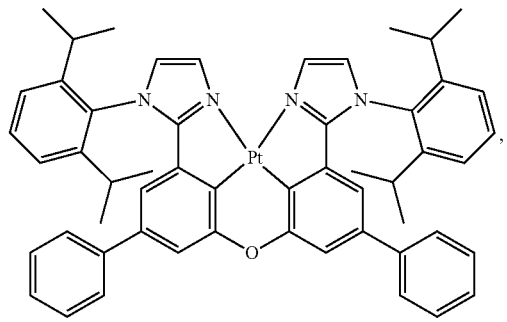

G1

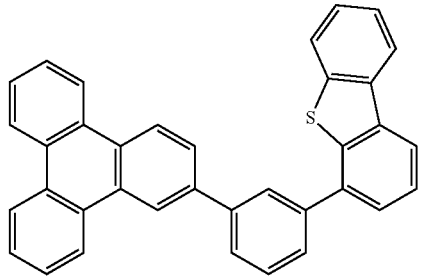

M1

Figure 6:
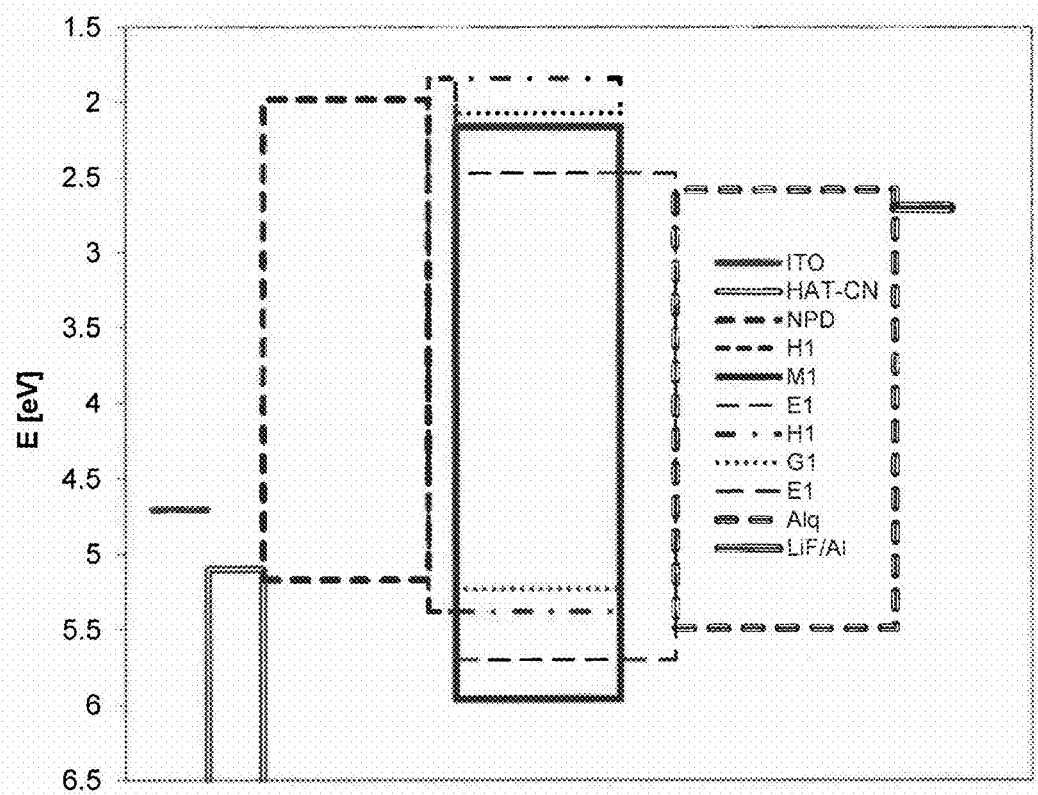
FIG. 6 shows the energy level diagram for an OLED using G1 as an emitting compound.

Table 1 shows the T1, HOMO, and LUMO energy levels of B2. Additionally, FIG. 6 depicts the energy level diagram of Model Device 3.

Eight comparative examples were constructed. These comparative devices are different from Model Device 3 in that they lack one or more of the four different components and/or use a different host material. Table 5A details the difference between these three comparative examples and Model Device 3. Table 5B details the output of Model Device 2 and the comparative examples. These comparative examples demonstrates the inferior performance of the structures with one or more components missing.

TABLE 5A

Experimental Data for Model Device 3 and Comparative Examples

G1 Green Emitter

| Example | EBL [Å] | Host | Electron transporting compound | Hole transporting compound | G1 [%] | HBL | 1931 CIE x | 1931 CIE y |
|---|---|---|---|---|---|---|---|---|
| CE 11 | H1 50 Å | M1 | — | — | 12 | E1 100 Å | 0.288 | 0.664 |
| CE 12 | H1 50 Å | E1 | — | — | 12 | E1 100 Å | 0.300 | 0.656 |
| CE 13 | H1 50 Å | H1 | — | — | 12 | E1 100 Å | 0.280 | 0.666 |
| CE 14 | H1 50 Å | M1 | — | H1 15% | 10 | E1 100 Å | 0.279 | 0.666 |
| CE 15 | H1 50 Å | M1 | E1 25% | — | 10 | E1 100 Å | 0.288 | 0.662 |
| CE 16 | H1 50 Å | E2 | — | H1 15% | 10 | E1 100 Å | 0.295 | 0.657 |
| CE 17 | H1 50 Å | M1 | E1 25% | H1 10% | 5 | — | 0.281 | 0.662 |
| Model Device 3 | H1 50 Å | M1 | E1 25% | H1 10% | 5 | E1 100 Å | 0.293 | 0.660 |
| CE 18 | — | M1 | E1 25% | H1 10% | 5 | E1 100 Å | 0.282 | 0.662 |

TABLE 5B

Experimental Data for Model Device 3 and Comparative Examples

|  | | | At 1,000 nits | | |
|---|---|---|---|---|---|
| Example | λ max [nm] | FWHM [nm] | Voltage [V] | Relative LE [%] | Relative EQE [%] | Relative LT [%] |
| CE 11 | 520 | 22 | 4.8 | 94 | 94 | 64 |
| CE 12 | 520 | 22 | 4.9 | 72 | 72 | 22 |
| CE 13 | 519 | 22 | 4.1 | 40 | 41 | 6 |
| CE 14 | 518 | 20 | 4.3 | 99 | 102 | 31 |
| CE 15 | 520 | 21 | 4.7 | 91 | 92 | 72 |
| CE 16 | 520 | 22 | 4.3 | 94 | 95 | 56 |
| CE 17 | 519 | 22 | 4.6 | 28 | 29 | 56 |
| Model Device 3 | 519 | 22 | 4.4 | 100 | 100 | 100 |
| CE 18 | 519 | 22 | 4.6 | 69 | 70 | 90 |

Comparative Examples

Shallow Homo Emitter (Ir(ppy))

Figure 7:
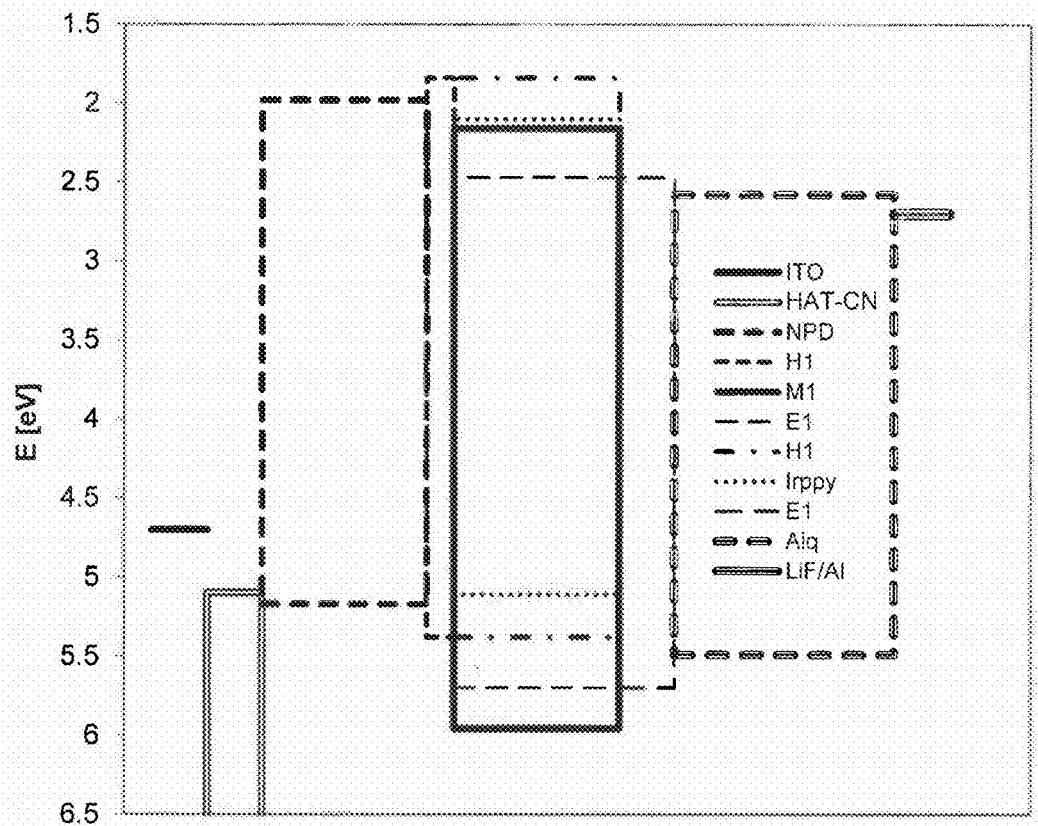
FIG. 7 shows the energy diagram for a comparative OLED using Ir(ppy) as the emitting compound.

Comparative Example 26 is similar to Model Devices 3 except that it does not use a deep HOMO emitter, but uses a shallow HOMO emitter Ir(ppy). FIG. 7 details the energy diagram for this comparative example.

Additionally, comparative devices CE19-CE25 and CE 27 were constructed using Ir(ppy) as the emitter. While comparative example 26 contains all of the four components, CE19-CE 25 and CE 27 are each missing one or more of the components. Table 6A details the differences between these comparative examples. Table 6B details the output of these comparative examples.

As can be seen in Table 6A, the structure in CE 26, with all four components (the host, electron transporting compound in the emissive layer, the hole transporting compound in the emissive layer, the electron blocking layer, and the hole blocking layer) is not the optimal structure for this emitter. CE27, without an electron blocking layer, demonstrates superior performance in terms of lifetime compared to CE26.

TABLE 6A

Experimental Data for Comparative Examples with Ir(ppy)

G1 Green Emitter

| Example | EBL [Å] | Host | Electron transporting compound | Hole transporting compound | Ir(ppy) [%] | HBL | 1931 CIE x | 1931 CIE y |
|---|---|---|---|---|---|---|---|---|
| CE 19 | H1 50 Å | M1 | — | — | 12 | E1 100 Å | 0.304 | 0.632 |
| CE 20 | H1 50 Å | E1 | — | — | 12 | E1 100 Å | 0.312 | 0.629 |
| CE 21 | H1 50 Å | H1 | — | — | 12 | E1 100 Å | 0.292 | 0.637 |
| CE 22 | H1 50 Å | M1 | — | H1 15% | 10 | E1 100 Å | 0.304 | 0.636 |
| CE 23 | H1 50 Å | M1 | E1 25% | — | 10 | E1 100 Å | 0.309 | 0.634 |
| CE 24 | H1 50 Å | E2 | — | H1 15% | 10 | E1 100 Å | 0.314 | 0.631 |
| CE 25 | H1 50 Å | M1 | E1 25% | H1 10% | 5 | — | 0.285 | 0.635 |
| CE 26 | H1 50 Å | M1 | E1 25% | H1 10% | 5 | E1 100 Å | 0.296 | 0.634 |
| CE 27 | — | M1 | E1 25% | H1 10% | 5 | E1 100 Å | 0.289 | 0.634 |

TABLE 6B

Experimental Data for Comparative Examples with Ir(ppy)

|  | | | At 1,000 nits | | |
|---|---|---|---|---|---|
| Example | λ max [nm] | FWHM [nm] | Voltage [V] | Relative LE [%] | Relative EQE [%] | Relative LT [%] |
| CE 19 | 520 | 66 | 5.2 | 103 | 101 | 33 |
| CE 20 | 520 | 66 | 4.8 | 103 | 102 | 20 |
| CE 21 | 516 | 62 | 4.6 | 61 | 61 | 2 |
| CE 22 | 518 | 68 | 5.1 | 123 | 118 | 37 |
| CE 23 | 519 | 68 | 4.8 | 116 | 111 | 77 |
| CE 24 | 519 | 69 | 4.8 | 121 | 116 | 32 |
| CE 25 | 514 | 62 | 4.8 | 73 | 74 | 44 |
| CE 26 | 516 | 66 | 5.0 | 128 | 126 | 77 |
| CE 27 | 514 | 64 | 5.0 | 100 | 100 | 10 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A device comprising, in order:
an anode;
an electron blocking layer;
an organic light emissive layer;
a hole blocking layer;
a cathode;
wherein the organic light emissive layer comprises a first sub-layer, wherein the first sub-layer includes:
a host compound;
a first emitting compound with a HOMO of 5.2 eV or lower and a LUMO of 2.5 eV or higher, the first emitting compound capable of phosphorescence emission at room temperature;
a hole transporting compound; and
an electron transporting compound;
wherein less than 5% of the light emitted from the device is comprised of light emitted from the hole transporting compound, light emitted from the electron transporting compound and light emitted from the host.

2. The device of claim 1, wherein the electron blocking layer is in direct contact with the organic light emissive layer; and the hole blocking layer is in direct contact with the organic light emissive layer.

3. The device of claim 1, wherein the first sub-layer is the only layer in the organic light emissive layer.

4. The device of claim 1, wherein the organic light emissive layer comprises a second sub-layer, wherein the second sub-layer includes:
   a second host compound;
   a second emitting compound different from the first emitting compound;
   a second hole transporting compound; and
   a second electron transporting compound.

5. The device of claim 1, wherein the first emitting compound has a HOMO of 5.4 eV or lower.

6. The device of claim 1, wherein the hole transporting compound and the electron transporting compound are organic compounds.

7. The device of claim 1, wherein the hole transporting compound and the electron transporting compound are metal coordination compounds.

8. The device of claim 1, wherein the first emitting compound comprises a transition metal complex having at least one ligand or part of the ligand if the ligand is more than bidentate selected from the group consisting of:

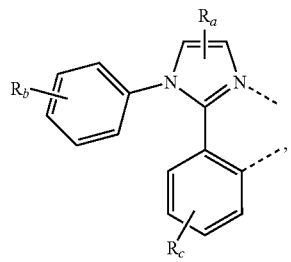

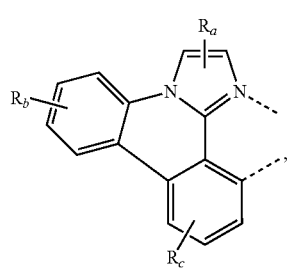

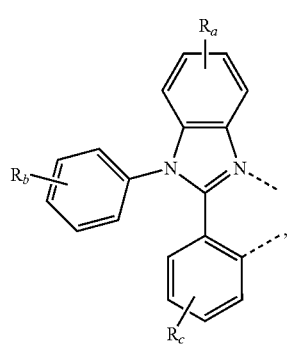

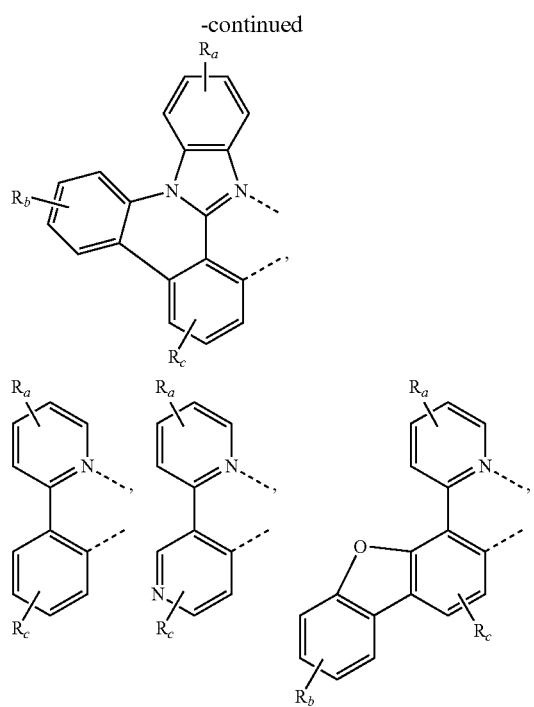

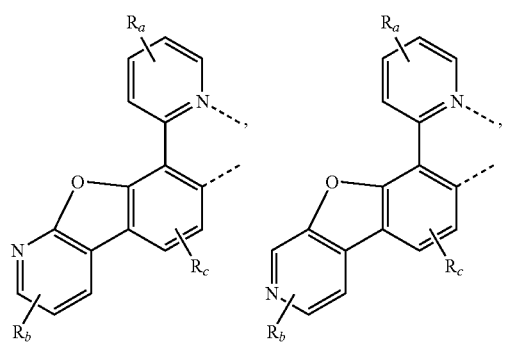

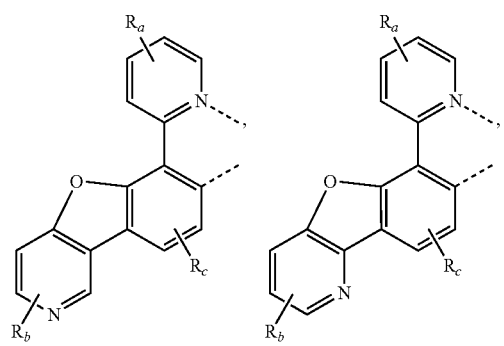

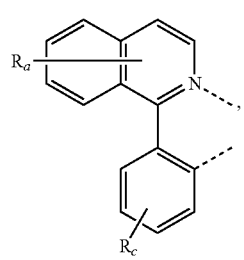

-continued

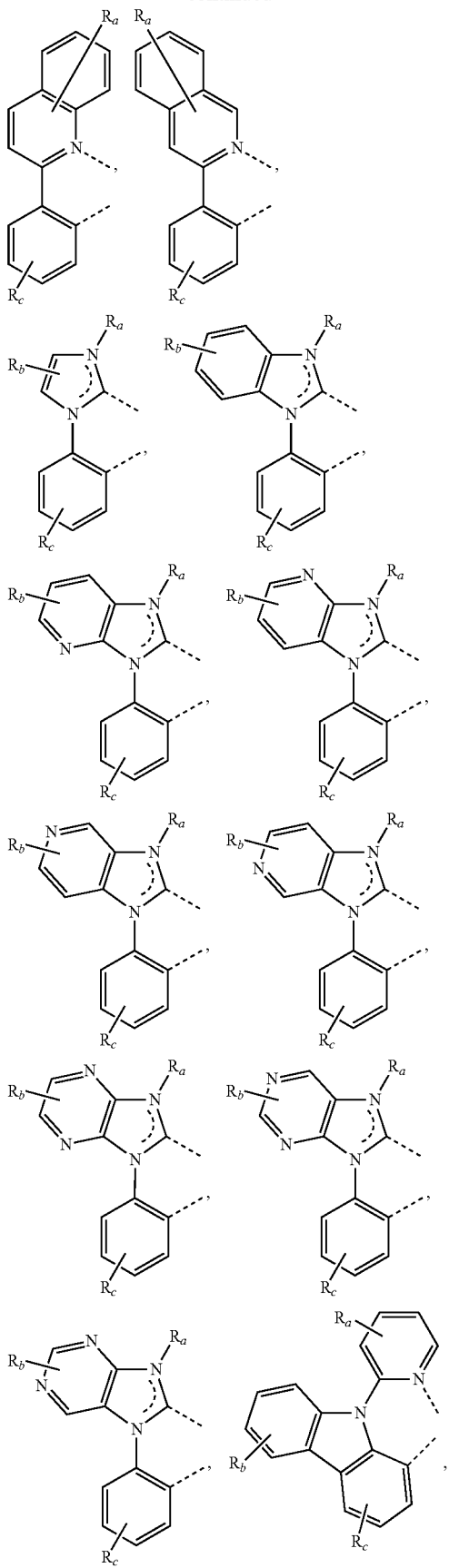

-continued

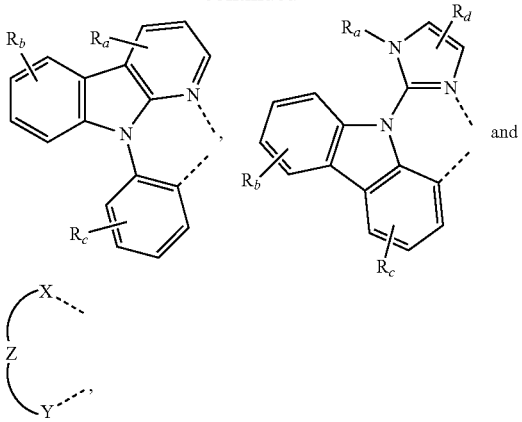

wherein $R_a$, $R_b$, $R_c$, and $R_d$ represents mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, phosphino, and combinations thereof;

wherein two adjacent substituents of $R_a$, $R_b$, $R_c$, and $R_d$ are optionally joined to form a fused ring or form a multidentate ligand;

wherein at least one of $R_c$ is an electron withdrawing group;

wherein X and Y are each independently selected from group consisting of pyrazole, tetrazole, thiazole, furan and pyridine;

wherein X and Y can be further substituted by one or more substituents selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxylic acids, ester, nitrile, isonitrile, sulfanyl, phosphino, and combinations thereof;

wherein Z is a group of formula BR'R"; and wherein R' and R" are independently selected from the group consisting of halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

9. The device of claim 1, wherein the first emitting compound is a Platinum tetradentate compound.

10. The device of claim 1,
wherein the electron blocking layer has a T1 at least 0.1 eV higher than a T1 of the emitting compound and a LUMO level at least 0.1 eV higher than a LUMO level of the emitting compound or the electron transporting compound;

wherein the hole blocking layer has a T1 at least 0.1 eV higher than the T1 of the emitting compound and a HOMO level at least 0.1 eV lower than a HOMO level of the emitting compound or the hole transporting compound;

wherein the electron transporting compound has a T1 at least 0.1 eV higher than the T1 of the emitting compound and the LUMO level of the electron transporting compound is at least 0.1 eV lower than a LUMO level of the hole transporting compound;

wherein the hole transporting compound has a T1 at least 0.1 eV higher than a T1 of the emitting compound and the HOMO level of the hole transporting compound is at least 0.1 eV higher than a HOMO level of the electron transporting compound; and wherein the host compound has:
- a T1 at least 0.1 eV higher than the T1 of the emitting compound;
- a HOMO level at least 0.3 eV lower than the HOMO level of the hole transporting compound; and
- a LUMO level at least 0.3 eV higher than the LUMO level of the electron transporting compound.

11. The device of claim 1, wherein the device comprises, in order:
the anode;
a hole transport layer;
the electron blocking layer;
the organic light emissive layer;
the hole blocking layer;
an electron transport layer; and
the cathode.

12. The device of claim 1, wherein the electron blocking layer has at least one of the following: a T1 at least 0.1 eV higher than a T1 of the first emitting compound, a LUMO level at least 0.1 eV higher than a LUMO level of the first emitting compound, or a LUMO level at least 0.1 eV higher than a LUMO level of the electron transporting compound.

13. The device of claim 1, wherein the hole blocking layer has at least one of the following: a T1 at least 0.1 eV higher than a T1 of the first emitting compound, a HOMO level at least 0.1 eV lower than a HOMO level of the first emitting compound, or a HOMO level at least 0.1 eV lower than a HOMO level of the hole transporting compound.

14. The device of claim 1, wherein the electron transporting compound has at least one of the following: a T1 at least 0.1 eV higher than a T1 of the first emitting compound, or a LUMO level at least 0.1 eV lower than a LUMO level of the hole transporting compound.

15. The device of claim 1, wherein the hole transporting compound has at least one of the following: a T1 at least 0.1 eV higher than a T1 of the first emitting compound, or a HOMO level at least 0.1 eV higher than a HOMO level of the electron transporting compound.

16. The device of claim 1, wherein the host compound has at least one of the following: a T1 at least 0.1 eV higher than a T1 of the first emitting compound, a HOMO level at least 0.3 eV lower than a HOMO level of the hole transporting compound, or a LUMO level at least 0.3 eV higher than a LUMO level of the electron transporting compound.

17. The device of claim 1, wherein a LUMO of the electron transporting compound is higher than 2.5 eV.

18. The device of claim 1, wherein a HOMO level of the hole transporting compound is lower than 5.2 eV.

19. The device of claim 1, wherein the device has a 19.9% EQE at 1000 nits.

20. The device of claim 1, wherein the first emitting compound is capable of one of: (1) red phosphorescent emission, having a peak wavelength in its emission spectrum in the range 590 nm to 700 nm; (2) yellow phosphorescent emission, having a peak wavelength in its emission spectrum in the range 550 nm to 590; (3) green phosphorescent emission, having a peak wavelength in its emission spectrum in the range 500 nm to 550 nm; and (4) blue phosphorescence emission, having a peak wavelength in its emission spectrum in the range 400 nm to 500 nm.

* * * * *